US011386558B2

(12) United States Patent
Shigeta et al.

(10) Patent No.: US 11,386,558 B2
(45) Date of Patent: Jul. 12, 2022

(54) MEDICAL IMAGE PROCESSING SYSTEM AND ENDOSCOPE SYSTEM

(71) Applicant: FUJIFILM Corporation, Tokyo (JP)

(72) Inventors: Norimasa Shigeta, Kanagawa (JP); Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/010,015

(22) Filed: Sep. 2, 2020

(65) Prior Publication Data
US 2020/0402235 A1 Dec. 24, 2020

Related U.S. Application Data

(63) Continuation of application No. PCT/JP2019/008567, filed on Mar. 5, 2019.

(30) Foreign Application Priority Data

Mar. 6, 2018 (JP) .............................. JP2018-040248

(51) Int. Cl.
G06T 7/00 (2017.01)
A61B 1/00 (2006.01)
A61B 5/00 (2006.01)

(52) U.S. Cl.
CPC .......... G06T 7/0012 (2013.01); A61B 1/0005 (2013.01); A61B 5/7221 (2013.01);
(Continued)

(58) Field of Classification Search
CPC ............... G06T 7/0012; G06T 2200/24; G06T 2207/10068; G06T 2207/20092;
(Continued)

(56) References Cited

U.S. PATENT DOCUMENTS

2006/0072118 A1* 4/2006 Chan .................. G01B 9/02069
356/495
2011/0230715 A1* 9/2011 Saito ..................... G06T 7/0012
600/109

(Continued)

FOREIGN PATENT DOCUMENTS

JP 2011-194028 A 10/2011
JP 2012-125402 A 7/2012
(Continued)

OTHER PUBLICATIONS

International Search Report issued in PCT/JP2019/008567; dated Jun. 4, 2019.
Written Opinion issued in PCT/JP2019/008567; dated Jun. 4, 2019.

*Primary Examiner* — Frank F Huang
(74) *Attorney, Agent, or Firm* — Studebaker & Brackett PC

(57) ABSTRACT

An oxygen saturation calculating unit calculates, based on an observation image, an oxygen saturation included in the observation target. A reliability calculating unit calculates, based on the observation image, reliability regarding the biological information. A reference value processing unit sets, for a measurement value indicative of the biological information of a measurement target in the observation target, a reference value serving as a reference for the biological information by using the reliability. A difference image generating unit calculates a difference value between the measurement value and the reference value and generates, based on the difference value, a difference image.

19 Claims, 26 Drawing Sheets

(52) U.S. Cl.
CPC ............. *G06T 2200/24* (2013.01); *G06T 2207/10068* (2013.01); *G06T 2207/20092* (2013.01)

(58) Field of Classification Search
CPC ... A61B 1/0005; A61B 5/7221; A61B 5/0075; A61B 5/6847; A61B 5/14551; A61B 5/1459; A61B 1/043; A61B 1/00009
See application file for complete search history.

(56) References Cited

U.S. PATENT DOCUMENTS

| | | | |
|---|---|---|---|
| 2011/0245642 A1* | 10/2011 | Minetoma | A61B 5/0084 600/324 |
| 2012/0053434 A1* | 3/2012 | Saito | A61B 1/063 600/324 |
| 2012/0130238 A1 | 5/2012 | Muraoka et al. | |
| 2012/0253157 A1 | 10/2012 | Yamaguchi et al. | |
| 2013/0018242 A1* | 1/2013 | Yamaguchi | A61B 5/14551 600/339 |
| 2014/0354794 A1 | 12/2014 | Imamura | |
| 2015/0208958 A1* | 7/2015 | Kaku | A61B 1/043 600/339 |
| 2016/0157763 A1* | 6/2016 | Tominaga | A61B 1/00009 600/317 |
| 2016/0183774 A1* | 6/2016 | Shiraishi | A61B 1/0684 600/317 |
| 2017/0258296 A1* | 9/2017 | Kaku | A61B 5/489 |
| 2018/0020903 A1* | 1/2018 | Saito | A61B 5/7235 382/128 |
| 2018/0033142 A1 | 2/2018 | Morita | |
| 2018/0271412 A1* | 9/2018 | Shigeta | A61B 5/14552 |
| 2018/0317754 A1* | 11/2018 | Yamamoto | A61B 1/00057 |
| 2019/0208985 A1* | 7/2019 | Fukuda | A61B 1/045 |
| 2019/0350505 A1* | 11/2019 | Fukuda | A61B 5/0075 |
| 2019/0357759 A1* | 11/2019 | Yamamoto | A61B 1/0638 |
| 2019/0374093 A1* | 12/2019 | Endo | A61B 5/1032 |
| 2020/0352488 A1* | 11/2020 | Saito | A61B 5/1459 |
| 2020/0402235 A1* | 12/2020 | Shigeta | A61B 5/7221 |
| 2021/0306542 A1* | 9/2021 | Kulcke | A61B 5/443 |

FOREIGN PATENT DOCUMENTS

| | | |
|---|---|---|
| JP | 2012-213550 A | 11/2012 |
| WO | 2016/162925 A1 | 10/2016 |

* cited by examiner

MEDICAL IMAGE PROCESSING SYSTEM AND ENDOSCOPE SYSTEM

CROSS-REFERENCE TO RELATED APPLICATIONS

This application is a Continuation of PCT International Application No. PCT/JP2019/008567 filed on 5 Mar. 2019, which claims priority under 35 U.S.C § 119(a) to Japanese Patent Application No. 2018-040248 filed on 6 Mar. 2018. The above application is hereby expressly incorporated by reference, in its entirety, into the present application.

BACKGROUND OF THE INVENTION

1. Field of the Invention

The present invention relates to a medical image processing system and an endoscope system that obtain biological information such as an oxygen saturation of hemoglobin in the blood.

2. Description of the Related Art

In the medical field, diagnosis is typically made by using an endoscope system including a light source device, an endoscope, and a processor device. In recent years, a lesion part is being diagnosed on the basis of, in biological information, an oxygen saturation of hemoglobin in the blood (JP2012-213550A (corresponding to US2012/253157A1), JP2012-125402A, and JP2011-194028A (corresponding to US2011/230715A1)).

SUMMARY OF THE INVENTION

It is known that there is a difference in biological information (e.g., an oxygen saturation) between a normal part and an abnormal part (a lesion part such as cancer) in an observation target. Knowing about a difference in an oxygen saturation between a normal part and an abnormal part, a user can easily find an abnormal part. In light of this, in JP2011-194028A, a reference value is set for the oxygen saturation, which is a kind of biological information, and a difference value between the reference value and the oxygen saturation at each position is displayed by using simulated color. In JP2011-194028A, by setting the reference value for the normal part, on the basis of the simulated color for the difference value, the difference in the oxygen saturation between the normal part and the abnormal part can be known.

However, in a halation region or the like in the observation target, the reliability of the calculated biological information is low. If the reference value is set for such a region with low reliability of the biological information, the reliability of the difference value from the reference value is also low.

An object of the present invention is to provide a medical image processing system and an endoscope system that can appropriately set the reference value serving as a reference for a measurement value of the biological information even in a case where a region with low reliability of the biological information is present.

A medical image processing system according to the present invention includes an image acquiring unit, a biological information calculating unit, a reliability calculating unit, a reference value processing unit, and a difference image generating unit. The image acquiring unit acquires an observation image obtained by imaging an observation target. The biological information calculating unit calculates, based on the observation image, biological information included in the observation target. The reliability calculating unit calculates, based on the observation image, reliability regarding the biological information. The reference value processing unit sets, for a measurement value indicative of the biological information of a measurement target in the observation target, a reference value serving as a reference for the biological information by using the reliability. The difference image generating unit calculates a difference value between the measurement value and the reference value and generates, based on the difference value, a difference image.

According to the present invention, it is preferable to further include a biological information image generating unit and a reference value calculation region setting unit. The biological information image generating unit generates, based on the biological information, a biological information image that is an image indicative of the biological information. The reference value calculation region setting unit sets a reference value calculation region that is a target for calculating the reference value in the observation image or the biological information image. The reference value processing unit preferably includes a first reference value calculating unit that calculates, based on the biological information included in the reference value calculation region, the reference value. It is preferable that the reference value calculation region setting unit automatically set, based on the reliability, the reference value calculation region.

According to the present invention, it is preferable to further include a region appropriateness determining unit and an error generating unit. The region appropriateness determining unit determines that the reference value is appropriately set in the reference value calculation region if a representative value of the reliability included in the reference value calculation region is greater than or equal to a region determination threshold and determines that the reference value is not appropriately set in the reference value calculation region if the representative value of the reliability included in the reference value calculation region is less than the region determination threshold. The error generating unit generates, if it is determined that the reference value is not accurately set in the reference value calculation region, an error for reporting that the reference value is not accurately calculated.

The reference value processing unit preferably further includes a region setting prohibition control unit that performs region setting prohibition control to prohibit setting of the reference value calculation region for a low reliability region where the reliability is less than a first reliability threshold in the observation image or the biological information image. it is preferable to further include a display control unit that displays the low reliability region on a display unit. It is preferable that the reference value be a representative value of the biological information included in the reference value calculation region.

It is preferable that the first reference value calculating unit multiply the biological information included in the reference value calculation region by a weighting factor based on the reliability and perform addition to calculate the reference value. The reference value processing unit preferably includes a second reference value calculating unit that multiplies the biological information by a weighting factor based on the reliability and performs addition to calculate the reference value.

The reference value processing unit preferably includes a high reliability region setting unit that sets a plurality of high reliability regions in which the reliability is greater than or equal to each of second reliability thresholds, the second reliability thresholds being different from each other and set in advance, and a first candidate reference value calculating unit that calculates candidate reference values serving as candidates for the reference value from the biological information included in the respective high reliability regions.

It is preferable to further include a display control unit that displays the high reliability regions and the candidate reference values corresponding to the high reliability regions on a display unit, and a first reference value selecting unit that selects the reference value from among the candidate reference values displayed on the display unit.

A medical image processing system according to the present invention includes an image acquiring unit, a biological information calculating unit, a reference value processing unit, a difference image generating unit, and a biological information frequency distribution calculating unit. The image acquiring unit acquires an observation image obtained by imaging an observation target. The biological information calculating unit calculates, based on the observation image, biological information included in the observation target. The reference value processing unit sets, for a measurement value indicative of the biological information of a measurement target in the observation target, a reference value serving as a reference for the biological information. The difference image generating unit calculates a difference value between the measurement value and the reference value and generates, based on the difference value, a difference image. The biological information frequency distribution calculating unit calculates a frequency distribution of the biological information. The reference value processing unit includes a third reference value calculating unit that calculates, based on a first region excluding distribution, the reference value, the first region excluding distribution excluding a first distribution region where reliability of the biological information is low in the frequency distribution of the biological information.

The reference value processing unit preferably further includes a first region excluding distribution setting unit that sets a plurality of first region excluding distributions excluding a plurality of first distribution regions from the frequency distribution of the biological information, the first distribution regions being set where the reliability of the biological information is low in the frequency distribution of the biological information, and a second candidate reference value calculating unit that calculates, based on the first region excluding distributions, candidate reference values serving as candidates for the reference value.

It is preferable to further include a display control unit that displays the first region excluding distributions and the candidate reference values corresponding to the first region excluding distributions on a display unit, and a second reference value selecting unit that selects the reference value from among the candidate reference values displayed on the display unit.

A medical image processing system according to the present invention includes an image acquiring unit, a biological information calculating unit, a reference value processing unit, a difference image generating unit, and an arithmetic value frequency distribution calculating unit. The image acquiring unit acquires observation images in a plurality of frames obtained by imaging an observation target in different frames. The biological information calculating unit calculates an arithmetic value through arithmetic processing based on the observation images in the plurality of frames and calculates, from the calculated arithmetic value, biological information included in the observation target. The reference value processing unit sets, for a measurement value indicative of the biological information of a measurement target in the observation target, a reference value serving as a reference for the biological information by using reliability of the biological information. The difference image generating unit calculates a difference value between the measurement value and the reference value and generates, based on the difference value, a difference image. The arithmetic value frequency distribution calculating unit calculates a frequency distribution of the arithmetic value. The reference value processing unit includes a fourth reference value calculating unit that uses the arithmetic value as the reliability, and calculates, based on a second region excluding distribution, the reference value, the second region excluding distribution excluding a second distribution region having a specific arithmetic value in the frequency distribution of the arithmetic value.

The reference value processing unit further includes a second region excluding distribution setting unit that sets a plurality of second region excluding distributions excluding a plurality of second distribution regions from the frequency distribution of the biological information, the second distribution regions being set and having the specific arithmetic value in the frequency distribution of the arithmetic value, and a third candidate reference value calculating unit that calculates, based on the second region excluding distributions, candidate reference values serving as candidates for the reference value.

It is preferable to further include a display control unit that displays the second region excluding distributions and the candidate reference values corresponding to the second region excluding distributions on a display unit, and a third reference value selecting unit that selects the reference value from among the candidate reference values displayed on the display unit.

The reference value processing unit preferably includes a user setting unit that sets the reference value by using a user interface, and the reference value set by the user setting unit is adjusted by using the reliability.

It is preferable to further include a biological information image generating unit that generates, based on the biological information, a biological information image that is an image indicative of the biological information, a measurement region setting unit that sets a region of the measurement target as a measurement target region in the observation image or the observation images or the biological information image, and a measurement value calculating unit that calculates, based on the biological information included in the measurement target region, the measurement value.

An endoscope system according to the present invention includes an endoscope, an image acquiring unit, a biological information calculating unit, a reliability calculating unit, a reference value processing unit, and a difference image generating unit. The endoscope obtains an observation image by imaging an observation target. The image acquiring unit acquires the observation image obtained by imaging the observation target. The biological information calculating unit calculates, based on the observation image, biological information included in the observation target. The reliability calculating unit calculates, based on the observation image, reliability regarding the biological information. The reference value processing unit sets, for a measurement value indicative of the biological information of a measurement target in the observation target, a reference value serving as a reference for the biological information by using the reliability. The difference image generating unit calculates a difference value between the measurement value and the reference value and generates, based on the difference value, a difference image.

According to the present invention, it is possible to be able to appropriately set the reference value serving as a reference for a measurement value of the biological information even in a case where a region with low reliability of the biological information is present.

DESCRIPTION OF THE PREFERRED EMBODIMENTS

First Embodiment

Figure 1:
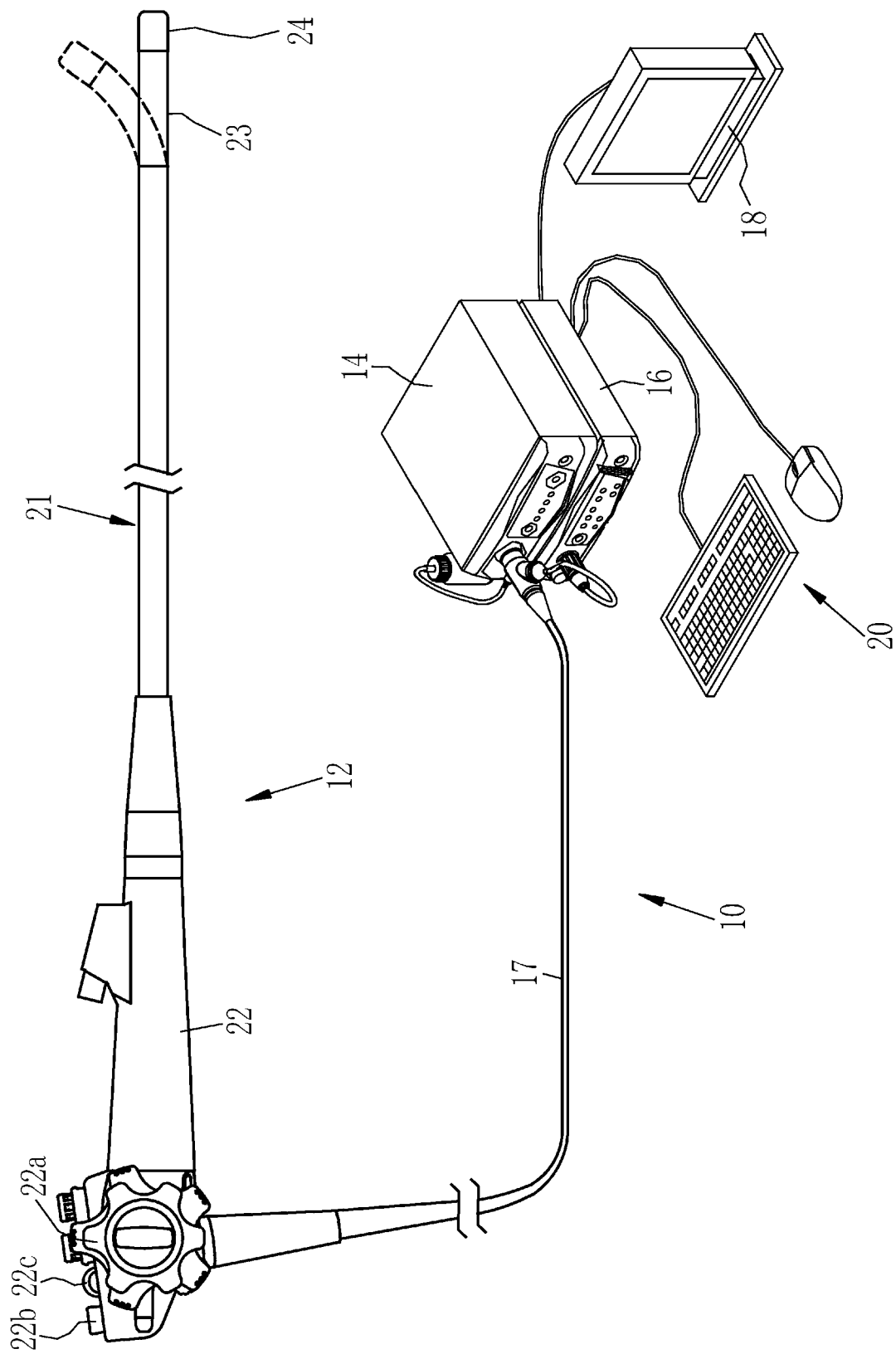
FIG. 1 is an external appearance view of an endoscope system.

As illustrated in FIG. 1, an endoscope system 10 according to a first embodiment has an endoscope 12, a light source device 14, a processor device 16, a monitor (display unit) 18, and a user interface 20. The endoscope 12 is optically connected to the light source device 14 and is also electrically connected to the processor device 16. The endoscope 12 has an insertion part 21 to be inserted into a subject, an operating unit 22 provided at the base end portion of the insertion part 21, and a bending part 23 and a tip part 24 provided at the distal end side of the insertion part 21. An operation of an angle knob 22a of the operating unit 22 causes the bending part 23 to bend. Along with this bending operation, the tip part 24 is oriented in a desired direction.

The operating unit 22 is provided with, in addition to the angle knob 22a, a mode switching switch (mode switching SW) 22b, a zoom operating unit 22c, and a freeze button (not illustrated) for storing a still image. The mode switching SW 22b is used for a switching operation between two kinds of modes: a usual observation mode and a biological information measurement mode. The usual observation mode is a mode in which a usual light image that is a full-color image of an observation target in a subject is displayed on the monitor 18. The biological information measurement mode is a mode in which an oxygen saturation image is displayed on the monitor 18. The oxygen saturation image is an image indicative of an oxygen saturation of hemoglobin in the blood, and the oxygen saturation is a kind of biological information included in an observation target. The zoom operating unit 22c is used for a zoom operation for driving a zoom lens 47 (see FIG. 2) in the endoscope 12 to zoom in the observation target.

Note that although the oxygen saturation is calculated in the biological information measurement mode, biological information other than the oxygen saturation may also be calculated. For example, it is considered that a blood vessel at a specific depth is extracted from an observation image obtained in the biological information measurement mode and a ratio of the blood vessel at the specific depth within a specific region of interest is calculated as a blood vessel density. The blood vessel density is a kind of biological information and is useful for diagnosis of an observation target. The blood vessel density may be displayed on the monitor 18 as a numeric value, and in addition, a blood vessel density image (a biological information image) may be displayed on the monitor 18. The blood vessel density image is an image using simulated color in accordance with the level of the blood vessel density.

The processor device 16 is electrically connected to the monitor 18 and the user interface 20. The monitor 18 displays an image such as a usual light image or an oxygen saturation image, and also information (hereinafter referred to as image information or the like) about such an image. The user interface 20 has a function of accepting an input operation such as function setting, and is specifically constituted by a keyboard, a mouse, and the like. Note that a recording unit (omitted from illustration) for recording image information or the like may also be connected to the processor device 16.

Figure 2:
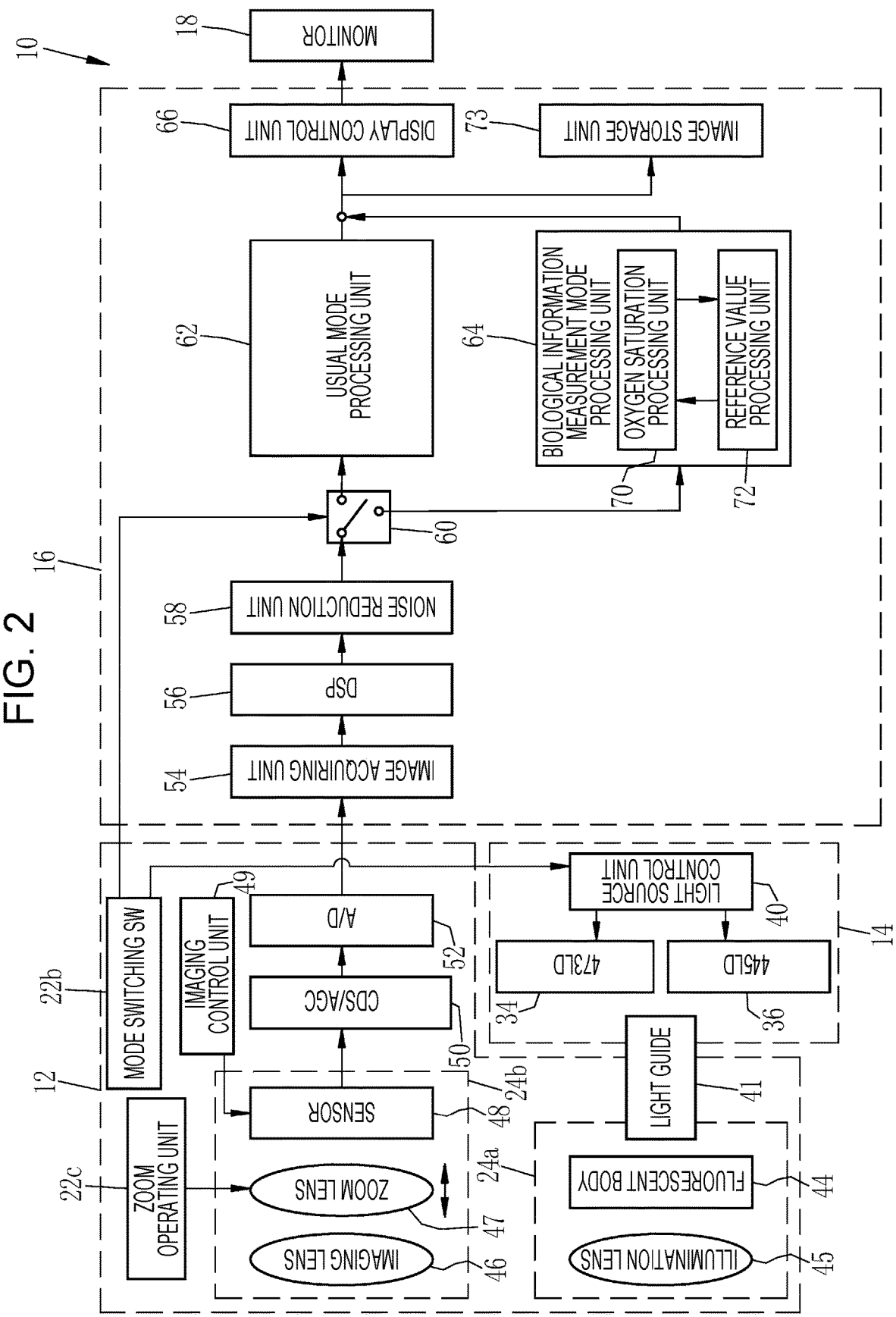
FIG. 2 is a block diagram of the endoscope system including a light source device having a laser light source.

As illustrated in FIG. 2, the light source device 14 includes, as light emission sources, a first blue laser light source (473 laser diode (LD) 34 that emits first blue laser light with a center wavelength of 473 nm and a second blue laser light source (445 LD) 36 that emits second blue laser light with a center wavelength of 445 nm. Light emission from the light sources 34 and 36 formed of semiconductor light emitting elements is individually controlled by a light source control unit 40. Thus, a light amount ratio between emission light from the first blue laser light source 34 and emission light from the second blue laser light source 36 is changeable.

In the usual observation mode, the light source control unit 40 turns on the second blue laser light source 36. In contrast, in the biological information measurement mode, the light source control unit 40 alternately turns on the first blue laser light source 34 and the second blue laser light source 36 at an interval of one frame. Note that a half-width of the first and second blue laser light is preferably about ±10 nm. In addition, for the first blue laser light source 34 and the second blue laser light source 36, an InGaN-based laser diode of a broad area type can be used, and also an InGaNAs-based laser diode or a GaNAs-based laser diode can be used. Furthermore, as the above light sources, a light emitting body such as a light emitting diode may also be used.

The first and second blue laser light emitted from the light sources 34 and 36 enters a light guide (LG) 41 through optical members such as a condensing lens, an optical fiber, and an optical multiplexer (none of which is illustrated). The light guide 41 is incorporated in the endoscope 12 and a universal cord 17 (see FIG. 1) that connects the light source device 14 and the endoscope 12. The first and second blue laser light from the light sources 34 and 36 propagates through the light guide 41 to the tip part 24 of the endoscope 12. Note that a multi-mode fiber can be used for the light guide 41. As an example, a small-diameter fiber cable having a core diameter of 105 μm, a clad diameter of 125 μm, and a diameter of Ø 0.3 to 0.5 mm including a protective layer serving as an outer skin can be used.

The tip part 24 of the endoscope 12 has an illumination optical system 24a and an imaging optical system 24b. In the illumination optical system 24a, a fluorescent body 44 and an illumination lens 45 are provided. The first and second blue laser light enters the fluorescent body 44 through the light guide 41. The fluorescent body 44 emits fluorescence by being irradiated with the first or second blue laser light. In addition, part of the first or second blue laser light directly passes through the fluorescent body 44. The observation target is irradiated with light emitted from the fluorescent body 44 through the illumination lens 45.

Figure 3:
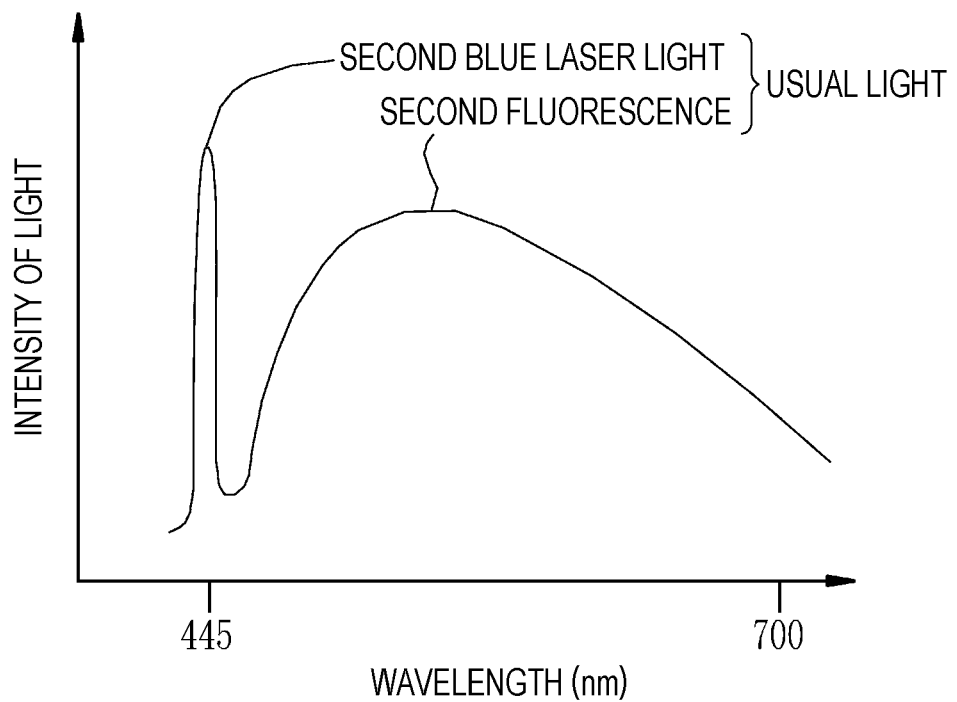
FIG. 3 is a graph illustrating the spectrum of light emitted in a usual observation mode.

In the usual observation mode, since the second blue laser light enters the fluorescent body 44, the observation target is irradiated with usual light with the spectrum illustrated in FIG. 3. This usual light is composed of the second blue laser light and green to red second fluorescence that is excited by the second blue laser light and emitted from the fluorescent body 44. Thus, the wavelength range of the usual light covers the entire visible light.

Figure 4:
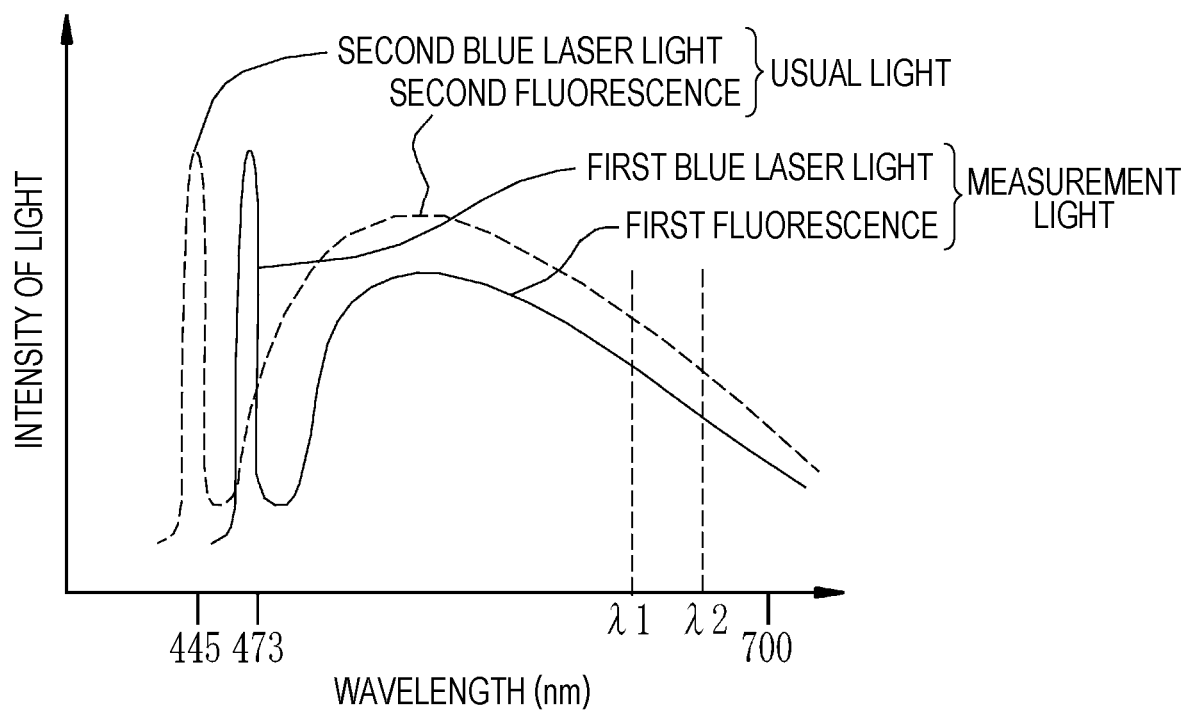
FIG. 4 is a graph illustrating the spectra of light emitted in a biological information measurement mode.

On the other hand, in the biological information measurement mode, since the first blue laser light and the second blue laser light alternately enter the fluorescent body 44, the observation target is alternately irradiated with measurement light and the usual light with the spectra illustrated in FIG. 4. The measurement light is used for measuring an oxygen saturation and is composed of the first blue laser light and green to red first fluorescence that is excited by the first blue laser light and emitted from the fluorescent body 44. Thus, the wavelength range of the measurement light covers the entire visible light. The usual light is the same as the usual light used for irradiation in the usual observation mode.

The first fluorescence and the second fluorescence have substantially the same waveform (form of spectrum) and have the same ratio between the intensity of the first fluorescence ($I1(\lambda)$) and the intensity of the second fluorescence ($I2(\lambda)$) (hereinafter referred to as an inter-frame intensity ratio) at any wavelength $\lambda$. For example, $I2(\lambda 1)/I1(\lambda 1)=I2(\lambda 2)/I1(\lambda 2)$. The inter-frame intensity ratio $I2(\lambda)/I1(\lambda)$ affects the calculation accuracy of the oxygen saturation, and thus, the light source control unit 40 performs control so as to maintain a preset reference inter-frame intensity ratio with high accuracy.

Note that as the fluorescent body 44, it is preferable to use one including a plurality of types of fluorescent bodies (e.g., YAG-based fluorescent body or a fluorescent body such as BAM ($BaMgAl_{10}O_{17}$)) that absorb part of the first and second blue laser light to be excited and emit green to red light. In addition, if a semiconductor light emitting element is used as an excitation light source for the fluorescent body 44 as in this embodiment, high-intensity measurement light and usual light can be obtained at high light emission efficiency. Furthermore, it is possible to adjust the intensity of each type of white light with ease and to suppress changes in color temperature and chromaticity to be small.

As illustrated in FIG. 2, the imaging optical system 24b of the endoscope 12 has an imaging lens 46, the zoom lens 47, and a sensor 48 (see FIG. 2). Reflected light from the observation target enters the sensor 48 through the imaging lens 46 and the zoom lens 47. Thus, a reflection image of the observation target is formed in the sensor 48. The zoom lens 47 moves between a telephoto end and a wide end in accordance with an operation of the zoom operating unit 22c. The movement of the zoom lens 47 between the telephoto end and the wide end causes the reflection image of the observation target to be enlarged or contracted.

The sensor 48 is a color imaging element and captures the reflection image of the observation target to output image signals. The sensor 48 is, for example, a charge coupled device (CCD) image sensor or a complementary metal-oxide semiconductor (CMOS) image sensor. In addition, the sensor 48 has RGB pixels provided with RGB color filters on an imaging surface and performs photoelectric conversion in the pixels of RGB colors to output image signals of three colors, RGB.

Figure 5:
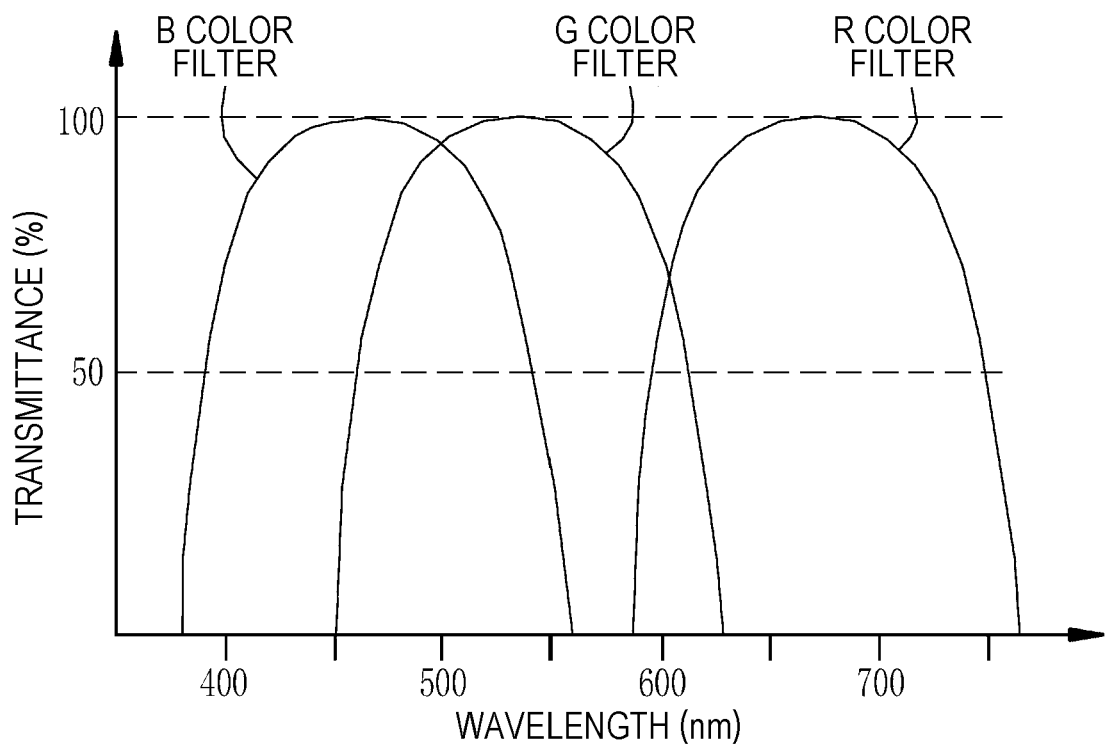
FIG. 5 is a graph illustrating spectral transmittances of RGB color filters.

As illustrated in FIG. 5, a B color filter has a spectral transmittance of 380 to 560 nm, a G color filter has a spectral transmittance of 450 to 630 nm, and a R color filter has a spectral transmittance of 580 to 760 nm. Thus, if the observation target is irradiated with usual light in the usual observation mode, the second blue laser light and part of the green component of the second fluorescence enter a B pixel, part of the green component of the second fluorescence enters a G pixel, and the red component of the second fluorescence enters a R pixel. Note that the intensity of the second blue laser light is much higher than that of the second fluorescence, and thus, most of the B image signals output from the B pixel is occupied by reflected light components of the second blue laser light.

On the other hand, if the observation target is irradiated with measurement light in the biological information measurement mode, the first blue laser light and part of the green component of the first fluorescence enter the B pixel, part of the green component of the first fluorescence enters the G pixel, and the red component of the first fluorescence enters the R pixel. Note that the intensity of the first blue laser light is much higher than that of the first fluorescence, and thus, most of the B image signals is occupied by reflected light components of the first blue laser light. Note that the incident light components of the RGB pixels when the observation target is irradiated with usual light in the biological information measurement mode are the same as those in the usual observation mode.

Note that as the sensor 48, a so-called complementary color image sensor including complementary color filters of C (cyan), M (magenta), Y (yellow), and G (green) on the imaging surface may be used. If a complementary color image sensor is used as the sensor 48, a color conversion unit that performs color conversion from image signals of four colors, CMYG, into image signals of three colors, RGB, may be provided in any of the endoscope 12, the light source device 14, and the processor device 16. Thus, even if a complementary color image sensor is used, image signals of three colors, RGB, can be obtained through color conversion from image signals of four colors, CMYG.

Figure 6:
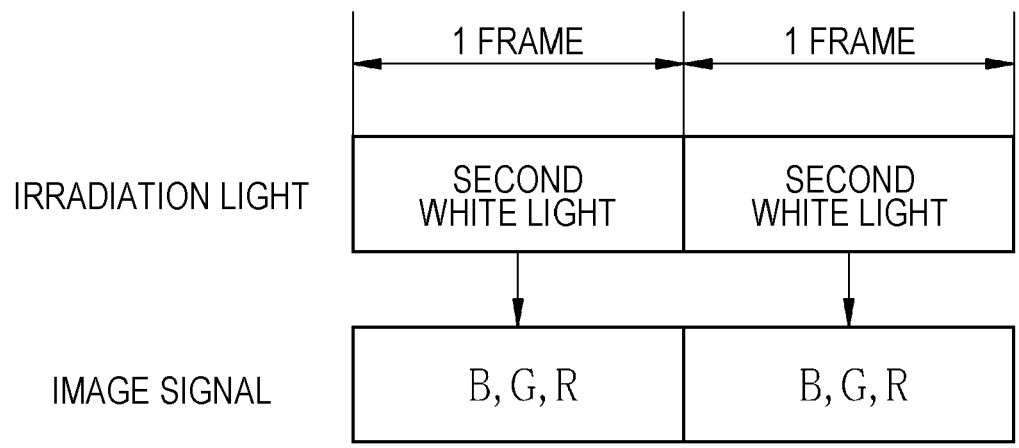
FIG. 6 illustrates imaging control in the usual observation mode in a case where the light source device having the laser light source is used.

An imaging control unit 49 controls imaging of the sensor 48. As illustrated in FIG. 6, in the usual observation mode, for each 1-frame period, the observation target illuminated with usual light is imaged by the sensor 48. Thus, RGB image signals are output from the sensor 48 in each frame.

Figure 7:
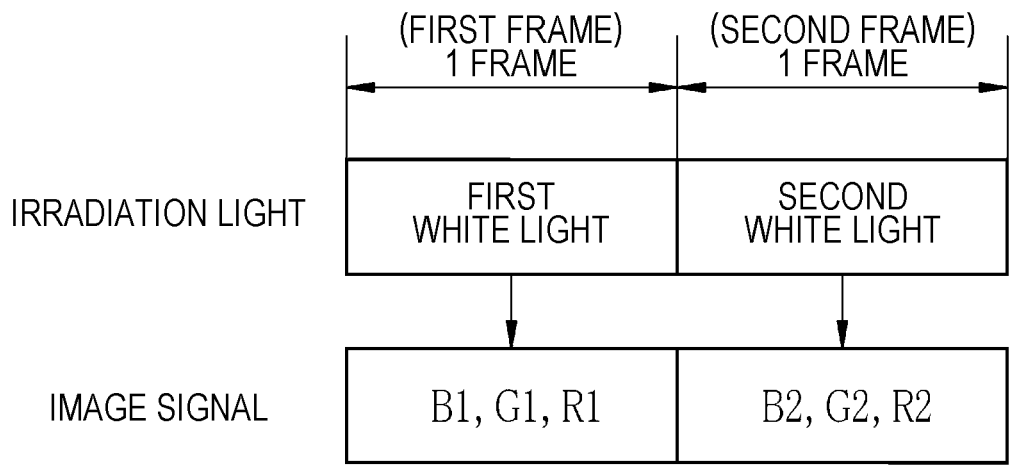
FIG. 7 illustrates imaging control in the biological information measurement mode in a case where the light source device having the laser light source is used.

Also in the biological information measurement mode, the imaging control unit 49 controls imaging of the sensor 48 as in the usual observation mode. However, in the biological information measurement mode, the observation target is alternately irradiated with measurement light and usual light in synchronization with imaging frames of the sensor 48. Thus, as illustrated in FIG. 7, the sensor 48 images the observation target with the measurement light in a first frame and images the observation target with the usual light in the subsequent second frame. Although the sensor 48 outputs RGB image signals both in the first frame and the second frame, the spectrum of depending white light differs. Thus, for distinction, the RGB image signals obtained by imaging with the measurement light in the first frame will be hereinafter referred to as a R1 image signal, a G1 image signal, and a B1 image signal, and the RGB image signals obtained by imaging with the usual light in the second frame will be hereinafter referred to as a R2 image signal, a G2 image signal, and a B2 image signal.

The image signals of the respective colors output from the sensor 48 are sent to a correlated double sampling (CDS)/automatic gain control (AGC) circuit 50 (see FIG. 2). The CDS/AGC circuit 50 performs correlated double sampling (CDS) or automatic gain control (AGC) on analog image signals output from the sensor 48. The image signals output from the CDS/AGC circuit 50 are converted into digital image signals by an A/D converter 52. The digital image signals are input to the processor device 16.

The processor device 16 includes an image acquiring unit 54, an image processing switching unit 60, a usual mode processing unit 62, a biological information measurement mode processing unit 64, and a display control unit 66. The image acquiring unit 54 acquires image signals input from the endoscope 12 as an image of the observation target. The processor device 16 includes a digital signal processor (DSP) 56 and a noise reduction unit 58. The DSP 56 performs digital signal processing on received image signals, such as color correction processing. The noise reduction unit 58 performs noise reduction processing by, for example, a moving average method or a median filter method, on image signals on which the color correction processing or the like is performed by the DSP 56. The image signals for which noise is reduced are input to the image processing switching unit 60.

If the mode switching SW 22b is set to the usual observation mode, the image processing switching unit 60 inputs the image signals to the usual mode processing unit 62. On the other hand, if the mode switching SW 22b is set to the biological information measurement mode, the image processing switching unit 60 inputs the image signals to the biological information measurement mode processing unit 64.

The usual mode processing unit 62 performs image processing for usual mode on the input image signals, such as color conversion processing, hue emphasizing processing, or structure emphasizing processing. The image signals subjected to the image processing for usual mode are input to the display control unit 66 as a usual observation image.

The biological information measurement mode processing unit 64 includes an oxygen saturation processing unit 70 and a reference value processing unit 72. On the basis of the input image signals, the oxygen saturation processing unit 70 calculates an oxygen saturation and generates an oxygen saturation image that is an image indicative of the calculated oxygen saturation. If an image generation mode is set to a difference image generation mode in the biological information measurement mode, for a measurement value indicating the oxygen saturation of a measurement target in the observation target, the reference value processing unit 72 sets a reference value as a reference for the oxygen saturation. Details of the oxygen saturation processing unit 70 and the reference value processing unit 72 will be described later. Note that mutual communication is possible between the oxygen saturation processing unit 70 and the reference value processing unit 72 so as to exchange various kinds of information.

The display control unit 66 performs control for displaying, on the monitor 18, image signals, various kinds of information, and the like input from the usual mode processing unit 62 or the biological information measurement mode processing unit 64. Under control of the display control unit 66, various images such as a usual light image and an oxygen saturation image are displayed, and in addition, various kinds of information is displayed to be superposed on the various images on the monitor 18.

Figure 8:
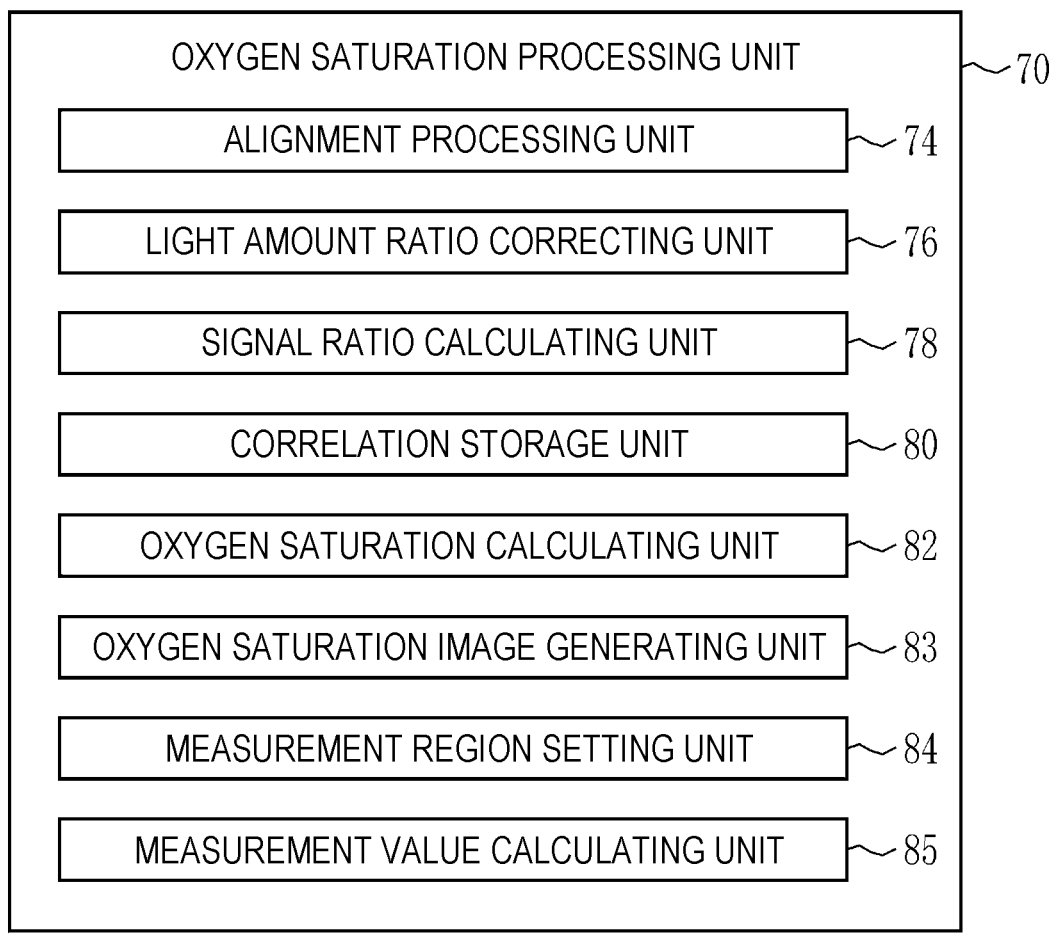
FIG. 8 is a block diagram of an oxygen saturation processing unit.

As illustrated in FIG. 8, the oxygen saturation processing unit 70 includes an alignment processing unit 74, a light amount ratio correcting unit 76, a signal ratio calculating unit 78, a correlation storage unit 80, an oxygen saturation calculating unit 82 (a biological information calculating unit), an oxygen saturation image generating unit 83 (a biological information image generating unit), a measurement region setting unit 84, and a measurement value calculating unit 85.

The alignment processing unit 74 performs alignment processing for the B1 image signal, the G2 image signal, and the R2 image signal to be used for calculating an oxygen saturation among image signals of two frames input to the oxygen saturation processing unit 70. The alignment processing is performed in this manner because misalignment may occur between frames as a result of movement of the observation target or the endoscope 12. Specifically, the B1 image signal in the first frame is aligned with the G2 image signal and the R2 image signal in the second frame. In the alignment processing, the B1 image signal in the first frame is compared with the B2 image signal in the second frame to calculate a movement amount of the observation target. On the basis of the calculated movement amount of the observation target, the observation target included in the B1 image signal is moved. Thus, the alignment processing is completed. Note that the movement amount is calculated from the B1 image signal in the first frame and the B2 image signal in the second frame because the B1 image signal and the B2 image signal include the same wavelength components and similar observation targets are captured, and the movement amount can be accurately calculated.

The light amount ratio correcting unit 76 performs light amount ratio correction processing on the B1 image signal, the G2 image signal, and the R2 image signal in accordance with variation in the light amount ratio between frames. In the light amount ratio correction processing, since image signals reflecting the variation in the light amount ratio between frames are the R1 image signal and the R2 image signal, from the R1 image signal and the R2 image signal, a light amount ratio correction factor Ck (the average value of the R2 image signal/the average value of the R1 image signal) is calculated. In addition, light amount ratio correction processing is performed on the G2 image signal and the R2 image signal according to the following equations to obtain the G2 image signal and the R2 image signal subjected to the light amount ratio correction processing. Note that the factor k represents the average value of the R2 image signal/the average value of the R1 image signal obtained when light amount control is ideally performed by the light source control unit 40.

Equations)

$$G2 \text{ image signal subjected to light amount ratio correction processing} = G2 \text{ image signal}/Ck \times k$$

$$R2 \text{ image signal subjected to light amount ratio correction processing} = R2 \text{ image signal}/Ck \times k$$

Among the image signals of two frames, which are subjected to the alignment processing and the light amount ratio correction processing, the B1 image signal, the G2 image signal, and the R2 image signal are input to the signal ratio calculating unit 78. The signal ratio calculating unit 78 calculates a signal ratio B1/G2 between the B1 image signal and the G2 image signal and a signal ratio R2/G2 between the G2 image signal and the R2 image signal for each pixel.

Figure 9:
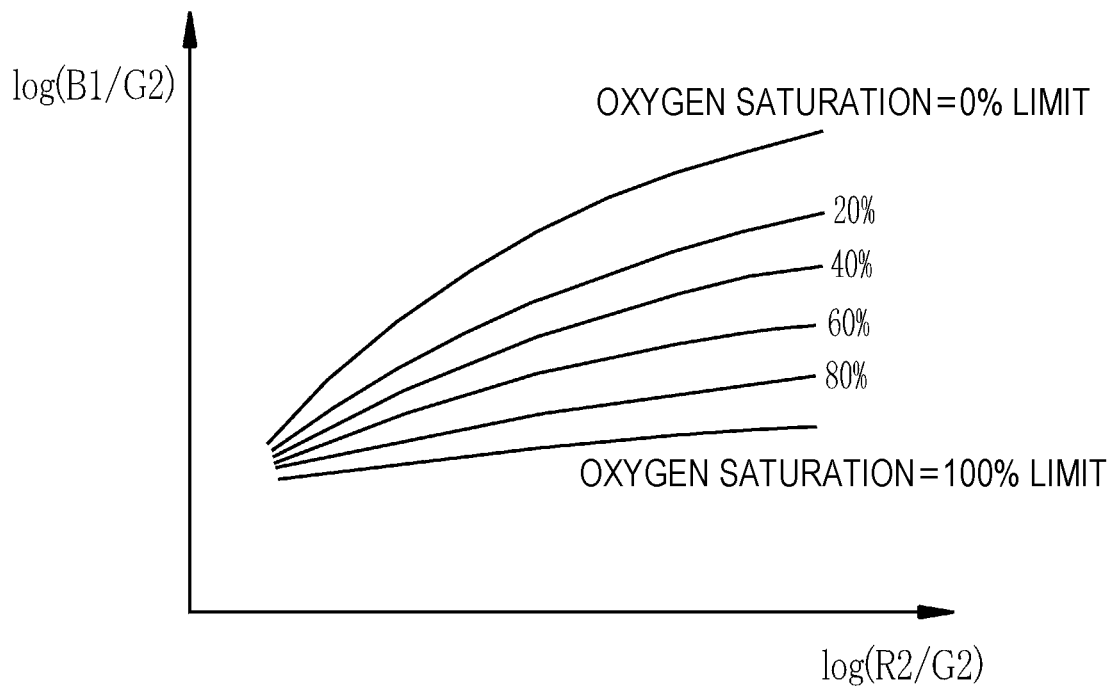
FIG. 9 is a graph illustrating a correlation between a signal ratio B1/G2 and an oxygen saturation and a correlation between a signal ratio R2/G2 and the oxygen saturation.

The correlation storage unit 80 stores a correlation between the signal ratio B1/G2 and the oxygen saturation and a correlation between the signal ratio R2/G2 and the oxygen saturation. The correlations are stored in the form of a two-dimensional table defining isopleths of the oxygen saturation in the two-dimensional space illustrated in FIG. 9. The positions and shapes of the isopleths for the signal ratio B1/G2 and the signal ratio R2/G2 are obtained in advance by physical simulation of light scattering, and the interval between the isopleths changes in accordance with the blood amount (the signal ratio R2/G2). Note that the correlation between the signal ratio B1/G2 and the oxygen saturation and the correlation between the signal ratio R2/G2 and the oxygen saturation are stored on a log scale.

Figure 10:
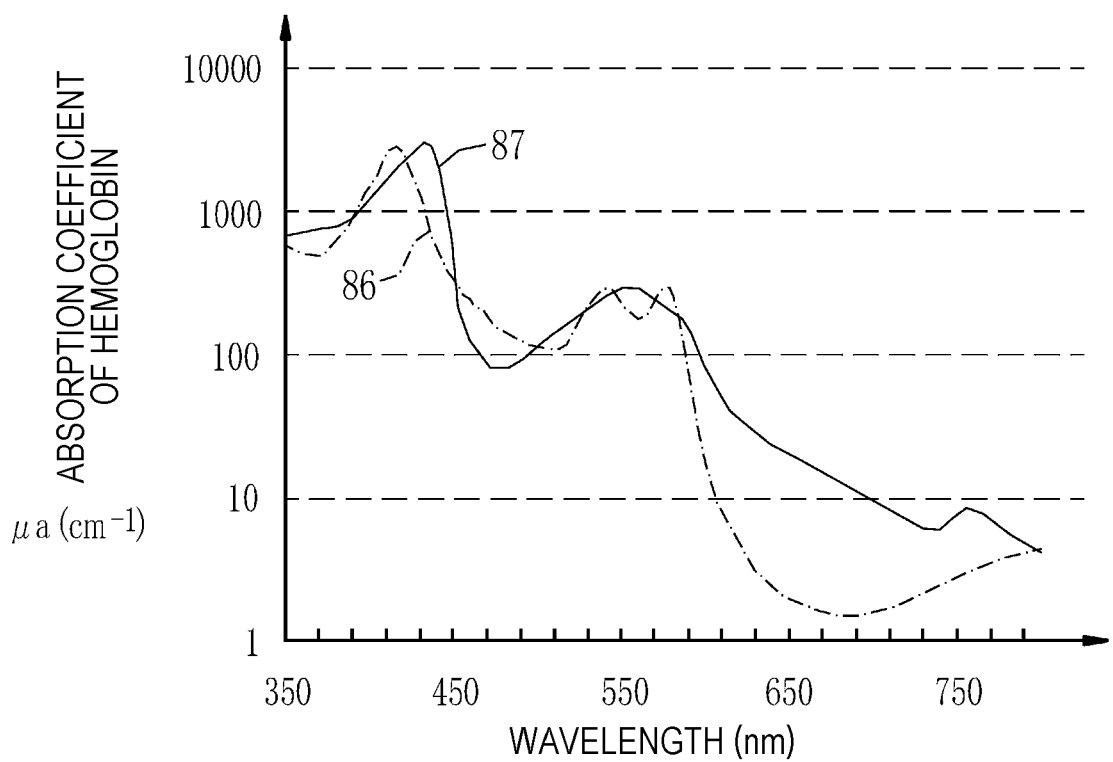
FIG. 10 is a graph illustrating absorption coefficients of oxidized hemoglobin and reduced hemoglobin.

Note that the above correlations closely relate to light absorption characteristics and light scattering characteristics of oxidized hemoglobin (graph 86) and reduced hemoglobin (graph 87) as illustrated in FIG. 10. For example, at 473 nm, which is the center wavelength of the first blue laser light where the difference in the absorption coefficient between oxidized hemoglobin and reduced hemoglobin is large, information of the oxygen saturation is easily handled. However, the B1 image signal including a signal corresponding to light at 473 nm is highly dependent on, not only the oxygen saturation, but also the blood amount. Accordingly, by using the signal ratios B1/G2 and R2/G2 obtained from, in addition to the B1 image signal, the R2 image signal corresponding to light that changes mainly dependent on the blood amount and the G2 image signal serving as reference signals for the B1 image signal and the R2 image signal, the oxygen saturation can be accurately obtained without being dependent on the blood amount.

Figure 11:
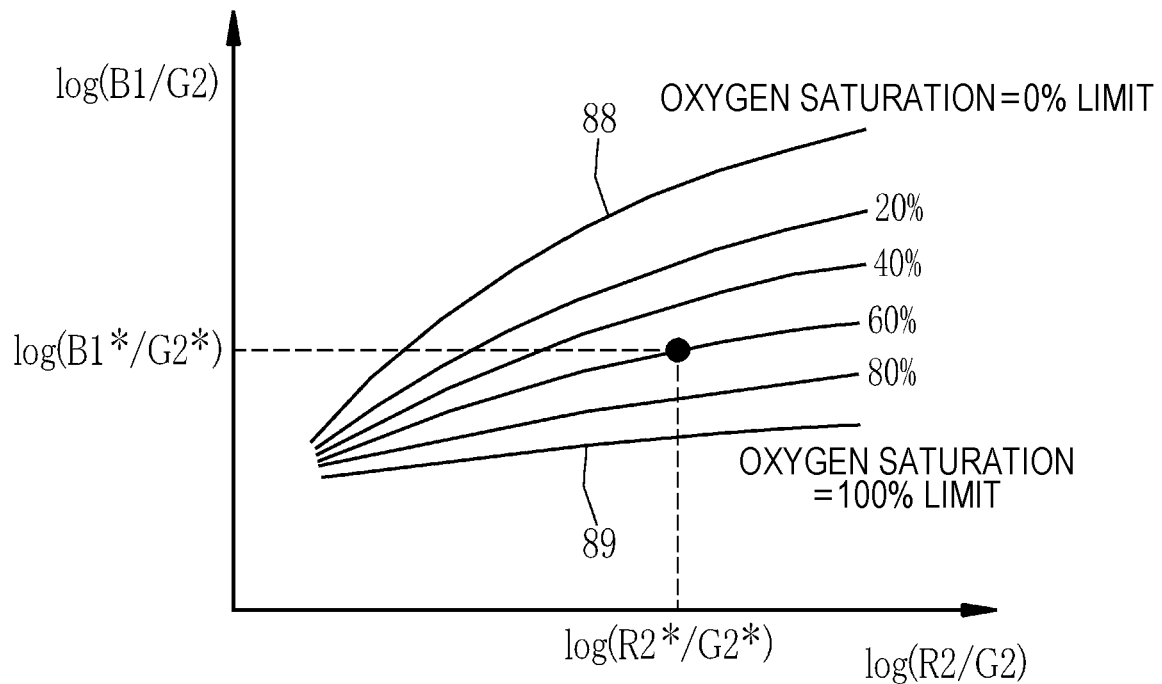
FIG. 11 illustrates a method for calculating the oxygen saturation.

Referring to the correlations stored in the correlation storage unit 80, the oxygen saturation calculating unit 82 calculates the oxygen saturation corresponding to the signal ratio B1/G2 and the signal ratio R2/G2 calculated by the signal ratio calculating unit 78 for each pixel. For example, in a case where the signal ratio B 1/G2 and the signal ratio R2/G2 at a specific pixel are B1*/G2* and R2*/G2*, respectively, as illustrated in FIG. 11, referring to the correlations, the oxygen saturation corresponding to the signal ratio B1*/G2* and the signal ratio R2*/G2* is "60%". Thus, the oxygen saturation calculating unit 82 calculates the oxygen saturation of this pixel as "60%".

Note that the signal ratio B1/G2 and the signal ratio R2/G2 are unlikely to become extremely high or extremely low. That is, the values of the signal ratio B1/G2 and the signal ratio R2/G2 are unlikely to become lower than a lower limit line 88 where the oxygen saturation is 0% or, on the contrary, higher than an upper limit line 89 where the oxygen saturation is 100%. However, if the calculated oxygen saturation is lower than the lower limit line 88, the oxygen saturation calculating unit 82 sets the oxygen saturation to 0%, and if the calculated oxygen saturation is higher than the upper limit line 89, the oxygen saturation calculating unit 82 sets the oxygen saturation to 100%. In addition, if the point corresponding to the signal ratio B1/G2 and the signal ratio R2/G2 is not between the lower limit line 88 and the upper limit line 89, the low reliability of the oxygen saturation at the pixel may be displayed, or the oxygen saturation is not necessarily calculated.

By using data of the oxygen saturation calculated by the oxygen saturation calculating unit 82, the B2 image signal, the G2 image signal, and the R2 image signal, the oxygen saturation image generating unit 83 generates an oxygen saturation image as a biological information image. The oxygen saturation image is an image indicative of the oxygen saturation. The generated oxygen saturation image is transmitted to the display control unit 66, and, if a capturing instruction is issued, the oxygen saturation image is stored in an image storage unit 73 (see FIG. 2). Note that if the oxygen saturation image is stored in the image storage unit 73, numeric value data of the oxygen saturation is preferably stored together. In this case, since the data amount becomes enormous if the entire numeric value data of the oxygen saturation is stored, a representative value (e.g., average value, maximum value, minimum value, or median value) of the oxygen saturation is preferably stored. In addition, not only the oxygen saturation image, but also a usual light image is also preferably stored in the image storage unit 73 in accordance with a capturing instruction.

For the oxygen saturation image generating unit 83, three kinds of image generation modes, which are a simulated color image generation mode, a combined image generation mode, and a difference image generation mode, are provided. In the simulated color image generation mode, a simulated color image that is an image indicative of the oxygen saturation by using simulated color corresponding to data of the oxygen saturation is generated. In the combined image generation mode, a combined image that is an image indicative of the oxygen saturation by using simulated color corresponding to the oxygen saturation is generated in a low oxygen region where the oxygen saturation is less than or equal to a fixed value in a usual light image. In the difference image generation mode, a difference image that is an image indicative of the oxygen saturation by using simulated color corresponding to a difference value between a measurement value indicative of the oxygen saturation of a measurement target and the reference value of the oxygen saturation serving as a reference for the measurement value is generated. Note that the above three kinds of image generation modes can be switched as appropriate by using the user interface 20. The oxygen saturation image generating unit in a case where the difference image generation mode is set corresponds to a "difference image generating unit" according to the present invention.

In the simulated color image generation mode, a simulated color image having a brightness signal Y and color difference signals Cr and Cb is generated. The G2 image signal for which visibility of a structure of the observation target, such as a blood vessel, is high is allocated to the brightness signal Y of the simulated color image. On the other hand, for the color difference signals Cr and Cb, a simulated color image color table (not illustrated) in which correspondence relations with the oxygen saturation is used. Thus, referring to the simulated color image color table, signal values corresponding to the oxygen saturation are allocated to the color difference signals Cr and Cb. For example, in the simulated color image color table, if the oxygen saturation is high, the signal value for Cr is set to be higher than that for Cb so as to increase redness. On the other hand, if the oxygen saturation is low, the signal value for Cb is set to be higher than that for Cr so as to increase blueness.

In the combined image generation mode, the B2 image signal, the G2 image signal, and the R2 image signal are multiplied by a gain in accordance with the oxygen saturation for each pixel, and a combined image is generated by using the B2 image signal, the G2 image signal, and the R2 image signal multiplied by the gain. For example, for a pixel in a high oxygen region where the oxygen saturation is greater than or equal to 60%, the B2 image signal, the G2 image signal, and the R2 image signal are multiplied by the same gain "1". On the other hand, for a pixel in a low oxygen region where the oxygen saturation is less than 60%, the B2 image signal is multiplied by a gain less than "1", and the G2 image signal and the R2 image signal are multiplied by a gain greater than or equal to "1". In this manner, a combined image is obtained in which the high oxygen region is represented by using the same color as that of a usual light image while the low oxygen region is represented by using simulated color in accordance with the oxygen saturation.

Figure 12:
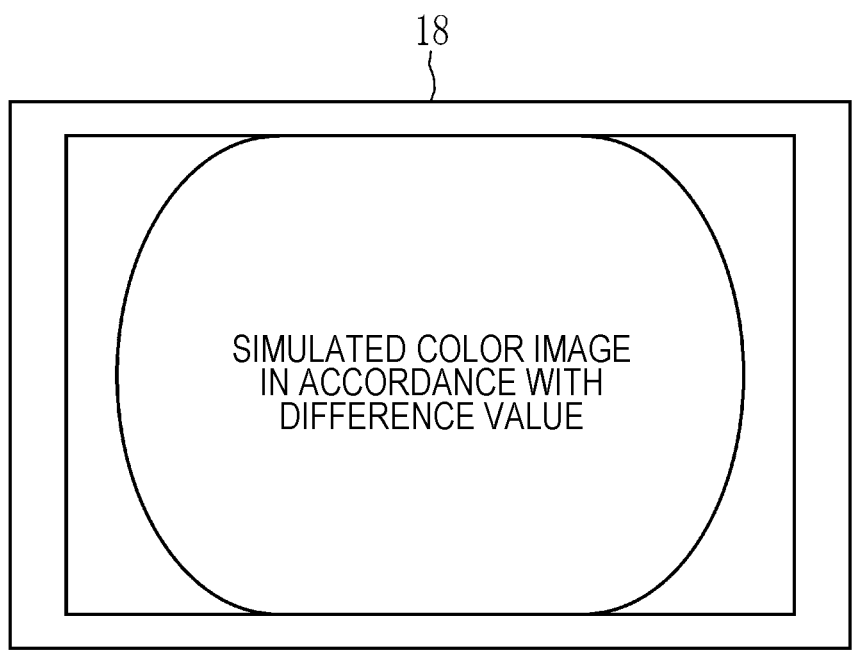
FIG. 12 is a diagram of an image illustrating a simulated color image in accordance with a difference value.
Figure 13:
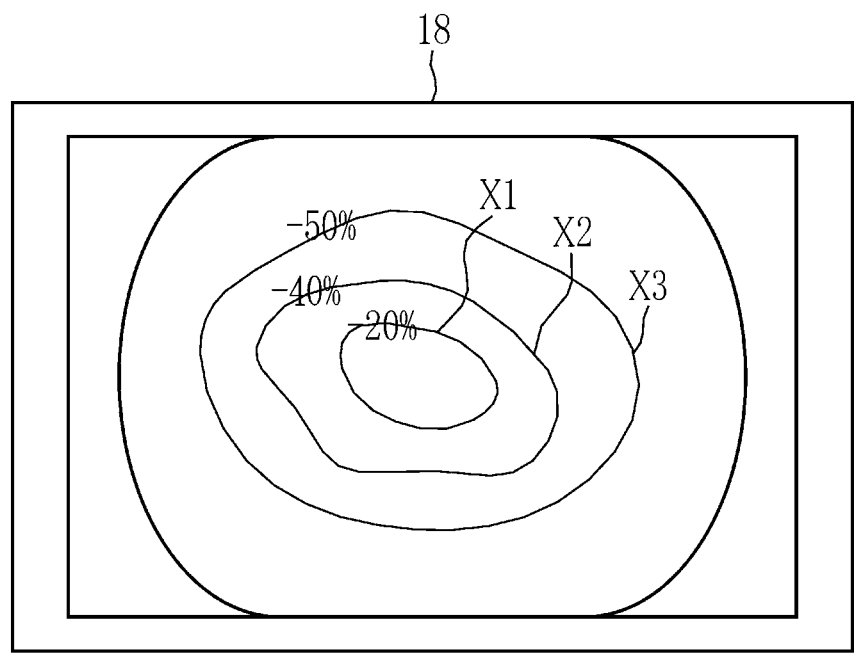
FIG. 13 is a diagram of an image illustrating an isopleth difference image.

In the difference image generation mode, a difference image is generated from a difference value between a measurement value and a reference value. The measurement value is the oxygen saturation calculated by the oxygen saturation calculating unit 82, and the reference value is set by the reference value processing unit 72. For the difference image, a representative value (e.g., average value, maximum value, or minimum value) of the difference value between the measurement value and the reference value in each pixel may be displayed as a numeric value. In addition, as illustrated in FIG. 12 for example, the difference image may be a simulated color difference image in which simulated color in accordance with the difference value between the measurement value of the oxygen saturation and the reference value in each pixel is displayed. Alternatively, as illustrated in FIG. 13, the difference image may be a contour difference image in which a contour in accordance with the difference value between the measurement value of the oxygen saturation and the reference value in each pixel is displayed. In the contour difference image, a contour X1 indicates that the difference value from the reference value is "−20%", a contour X2 indicates that the difference value from the reference value is "−40%", and a contour X3 indicates that the difference value from the reference value is "−50%". Note that the difference value is preferably the measurement value—the reference value. For example, in a case where the measurement value is "60%" and the reference value is "80%", the difference value is "−20%".

Figure 14:
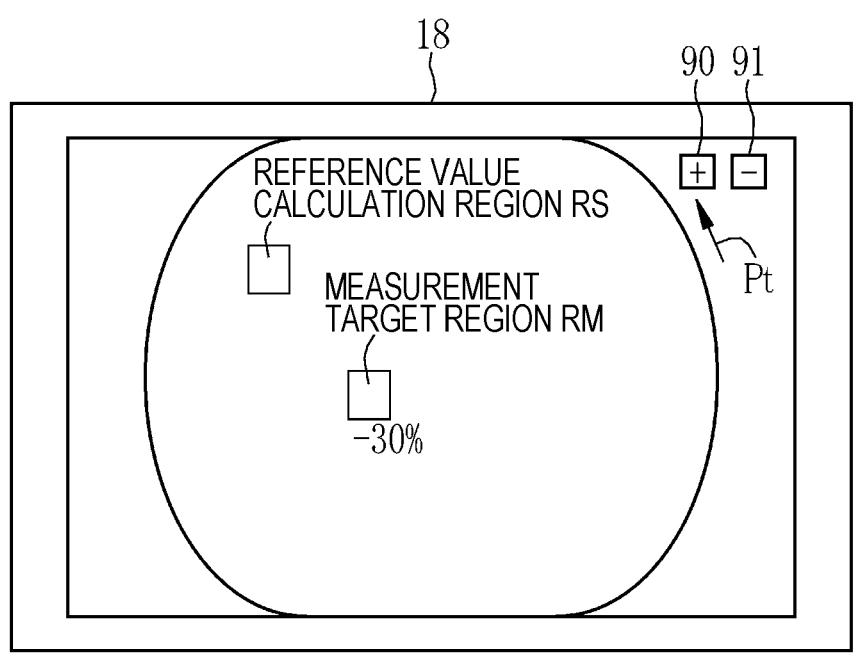
FIG. 14 is a diagram of an image illustrating a reference value calculation region RS and a measurement target region RM.

As illustrated in FIG. 14, the measurement region setting unit 84 sets, in a region other than a reference value calculation region RS, which will be described later, a measurement target region as a measurement target region RM, and the measurement value calculating unit 85 calculates a difference value between a representative value (e.g., average value, maximum value, or minimum value) of the oxygen saturation included in the measurement target region and the reference value. An image displaying the calculated difference value as a numeric value or the like may be set as the difference image of the measurement target region. The difference image of the measurement target region indicates that the difference value of the measurement target region RM is "−30%". Note that the measurement target region RM may be set within an image in which the reference value calculation region RS is set or may be set within an image obtained at a timing different from the timing for the image in which the reference value calculation region RS is set. In addition, for the reference value calculation region RS or the measurement target region RM, the location of the region is preferably followed in an image obtained at a timing different from the timing for the image in which these regions are set.

Figure 15:
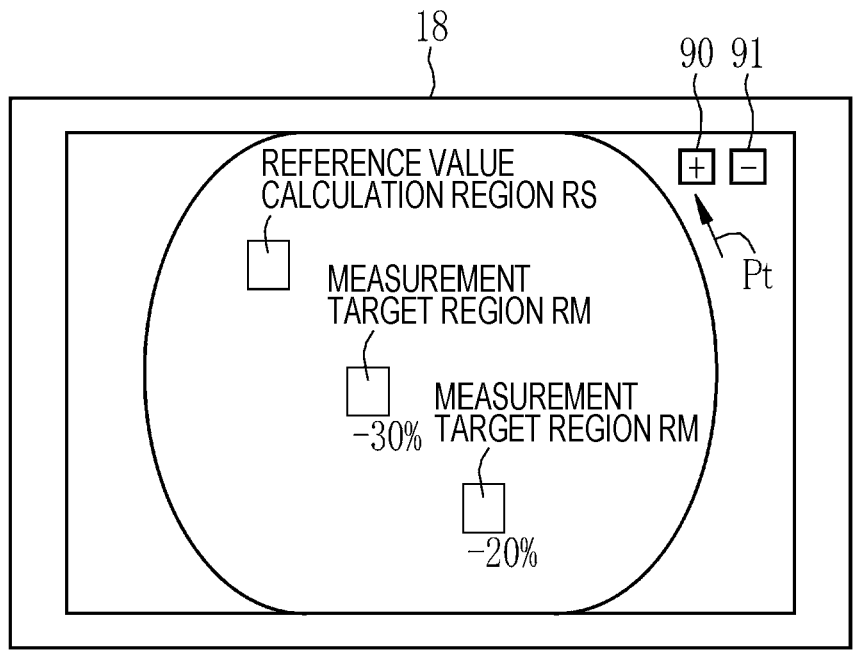
FIG. 15 is a diagram of an image illustrating the reference value calculation region RS and a plurality of measurement target regions RM.

In the difference image of the measurement target region, the measurement target region RM can be set by using the user interface 20. A plurality of measurement target regions RM can also be set. To increase the measurement target region RM, as illustrated in FIG. 15, if a "+" button 90 on the right side of the screen is clicked with a pointer Pt, the measurement target region RM is added on the screen. By moving the added measurement target region RM to the measurement target, the measurement target region RM is set. On the other hand, to decrease the measurement target region RM, if a "−" button 91 on the right side of the screen is clicked with the pointer Pt, the measurement target region RM is deleted from the screen.

Figure 16:
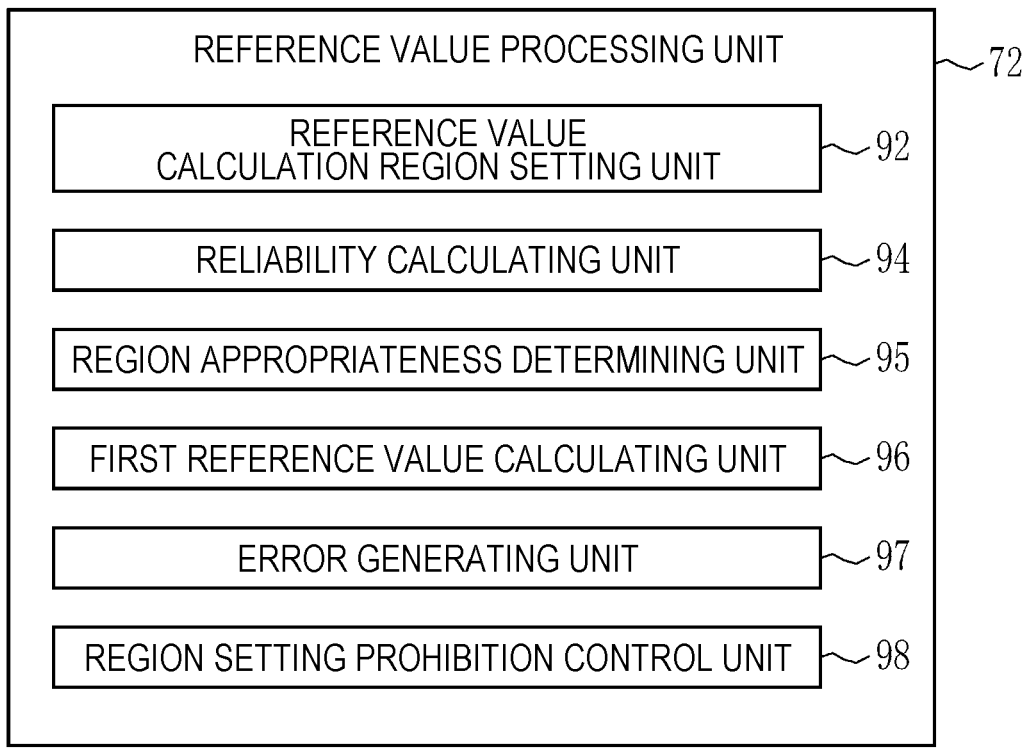
FIG. 16 is a block diagram illustrating functions of a reference value processing unit according to a first embodiment.
Figure 17A:
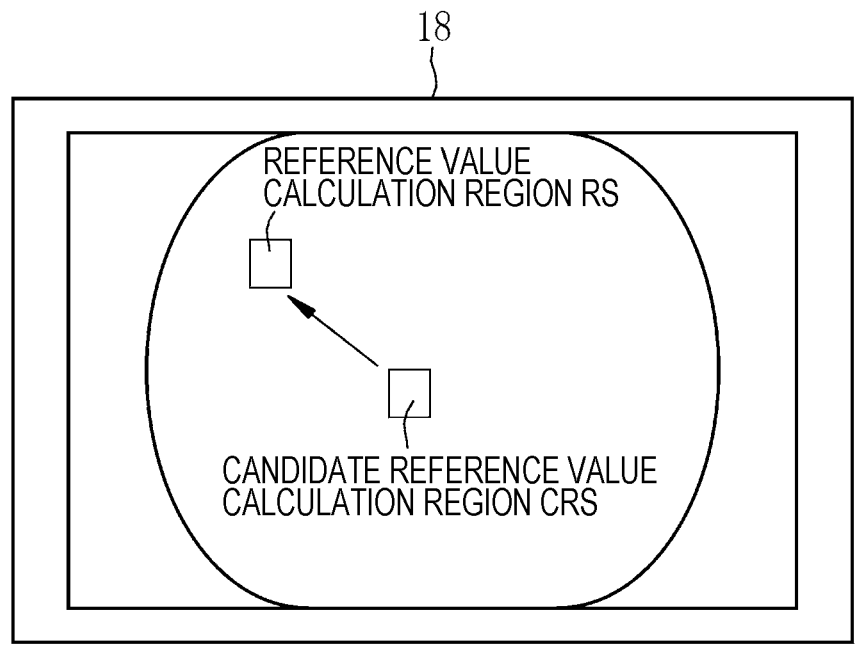
FIG. 17A is a diagram of an image illustrating the reference value calculation region RS and a candidate reference value calculation region CRS.

As illustrated in FIG. 16, the reference value processing unit 72 includes a reference value calculation region setting unit 92, a reliability calculating unit 94, a region appropriateness determining unit 95, a first reference value calculating unit 96, an error generating unit 97, and a region setting prohibition control unit 98. In a case where the image generation mode is set to the difference image generation mode in the biological information measurement mode, as illustrated in FIG. 17A, a reference value calculation region setting image for setting the reference value calculation region RS, which is a target for calculating the reference value, is displayed on the monitor 18, and also, the reference value calculation region setting unit 92 is started to prompt a user to set the reference value calculation region RS. In the reference value calculation region setting image, a candidate reference value calculation region CRS that is a candidate for the reference value calculation region RS is displayed. The user moves the candidate reference value calculation region CRS to a region that is desired to be a reference target in the observation target by using the user interface 20. When the candidate reference value calculation region CRS reaches the reference target, region confirmation processing is performed by using the user interface 20. Thus, setting of the reference value calculation region RS is completed.

Note that the reference value calculation region setting image may be, in addition to a usual light image, which is a kind of observation image, a simulated color image or a combined image, which is a biological information image. In addition, in a case where two or more of the usual light image, the simulated color image, and the combined image are displayed in parallel as reference value calculation region setting images, if the reference value calculation region RS is set in any of the images, the reference value calculation region RS may be displayed in the other images in cooperation. Furthermore, the shape of the reference value calculation region RS may be, in addition to a rectangle, a free-hand shape by using the user interface 20, such as a circle or an ellipse. In addition, the size of the reference value calculation region RS is preferably increased or decreased by, for example, a press-and-hold operation using the mouse in the user interface 20.

Alternatively, the reference value calculation region setting unit 92 may automatically set the reference value calculation region RS by using reliability, which will be described later, without a user. For example, for a region with reliability "1", the reference value calculation region setting unit 92 automatically sets the reference value calculation region RS.

In addition, in a case where the reference value calculation region RS is set in an image obtained at a specific timing, the reference value calculation region RS may be set in an image obtained at a timing different from the specific timing. In this case, the most recent reference value calculation region RS is employed. In a case where the reference value calculation region RS is set in a plurality of images obtained at different timings, a thumbnail may be displayed at a specific position on the monitor 18 for the image of the set reference value calculation region RS. In a case where a plurality of reference value calculation regions RS are set in the reference value calculation region setting image of one frame, among the plurality of reference value calculation regions RS, a reference value calculation region RS with the highest reliability, which will be described later, is preferably employed.

Figure 17B:
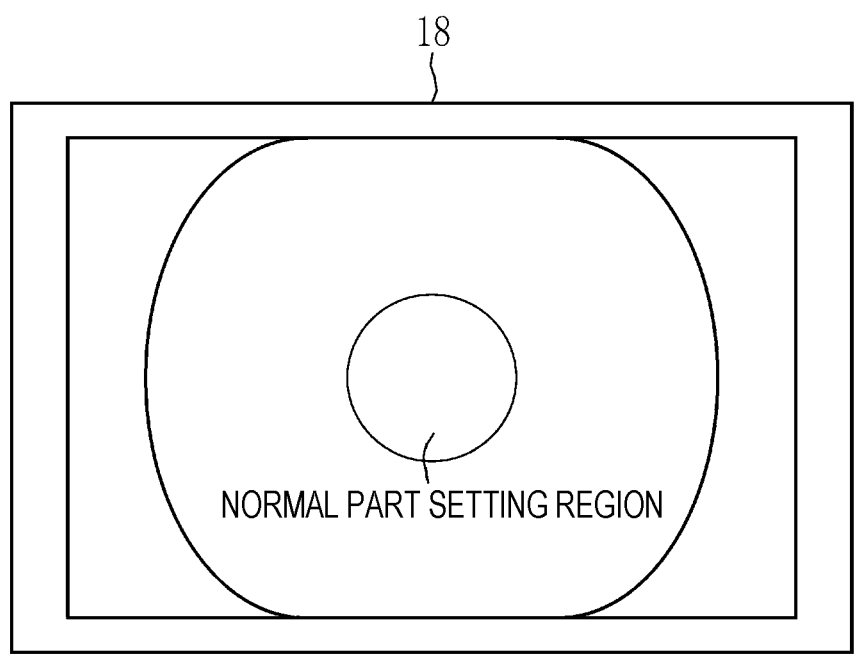
FIG. 17B is a diagram of an image illustrating a normal part setting region.

In addition, the reference value calculation region RS is preferably set for an image obtained while the endoscope 12 is being inserted into a body cavity. In this case, the reference value calculation region RS is set in a normal part of the observation target (preferably set as a default region). As a method for setting the normal part, as illustrated in FIG. 17B, a normal part setting region is provided at the center of the screen, and the endoscope 12 is operated so that the normal part falls within the normal part setting region. When the normal part falls within the normal part setting region, by operating the user interface 20, a region including the normal part is confirmed as the reference value calculation region RS. For this reference value calculation region RS, the reference value is calculated by the same procedure as that described later. Note that the reliability calculating unit 94, which will be described later, preferably calculates reliability of likelihood of the normal part. In this case, the oxygen saturation may be calculated on the basis of the reliability of likelihood of the normal part, and the reference value may be set on the basis of the calculated oxygen saturation.

The reliability calculating unit 94 calculates reliability regarding the oxygen saturation. The reliability is, for example, represented by a numeric value between "0" and "1", and the reliability is preferably higher as the numeric value is larger. As the reliability, for example, in a case where all of the B1 image signal, the G2 image signal, and the R2 image signal to be used for calculating the oxygen saturation, fall within an appropriate pixel value range, the reliability is preferably set to "1". In contrast, in a case where a pixel value of all of the B1 image signal, the G2 image signal, and the R2 image signal falls out of the appropriate pixel value range (lower than a lower limit or higher than an upper limit), the reliability is preferably set to "0". In addition, in a case where a pixel value of any of the B1 image signal, the G2 image signal, and the R2 image signal falls out of the appropriate pixel value range, in accordance with the magnitude of the pixel value, the reliability is preferably made close to "0" gradually. Furthermore, in a case where an arithmetic value in the biological information measurement mode obtained on the basis of any of the image signals obtained in the biological information measurement mode indicates the presence of a residue or a residual liquid, such as a yellow pigment, the reliability of the region is preferably decreased (e.g., the reliability is made lower than "1" and is decreased as the amount of the residue or the residual liquid is increased). In addition, in a case where an arithmetic value in the biological information measurement mode indicates the presence of a deep blood vessel, the reliability is preferably changed.

In a case where the reference value calculation region setting unit 92 sets the reference value calculation region RS, the region appropriateness determining unit 95 determines whether the reference value can be appropriately set in the set reference value calculation region RS on the basis of reliability included in the reference value calculation region RS. Specifically, if a representative value (e.g., average value, maximum value, or minimum value) of the reliability included in the reference value calculation region RS is greater than or equal to a region determination threshold, it is determined that the reference value can be appropriately set in the reference value calculation region RS. In this case, the first reference value calculating unit 96 calculates the reference value from an oxygen saturation included in the reference value calculation region RS.

Figure 18:
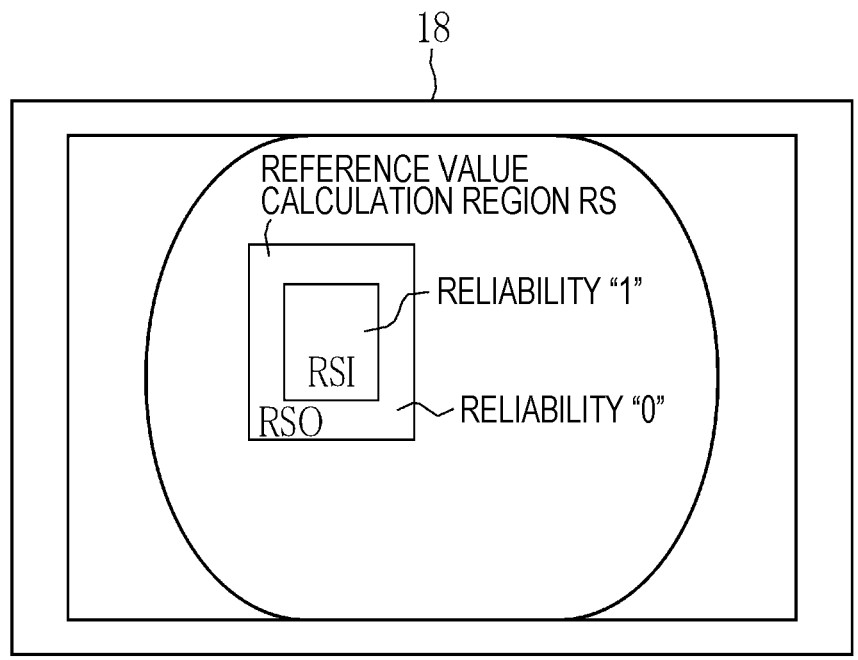
FIG. 18 illustrates a method for calculating a reference value obtained by multiplying an oxygen saturation included in the reference value calculation region RS by a weighting factor based on reliability and performing addition.

As a method for calculating the reference value, the first reference value calculating unit 96 preferably calculates, as the reference value, a representative value (e.g., average value, maximum value, or minimum value) of the oxygen saturation included in the reference value calculation region RS. The first reference value calculating unit 96 may multiply an oxygen saturation included in the reference value calculation region RS by a weighting factor based on the reliability and perform addition to calculate the reference value. For example, as illustrated in FIG. 18, if a weighting factor based on the reliability is set to "1" for an inner region RSI and a weighting factor based on the reliability is set to "0" for an outer region RSO in the reference value calculation region RS, the reference value is a value obtained by adding together a value obtained by multiplying the oxygen saturation included in the inner region RSI by "1" and a value obtained by multiplying the oxygen saturation included in the outer region RSO by "0".

Figure 19:
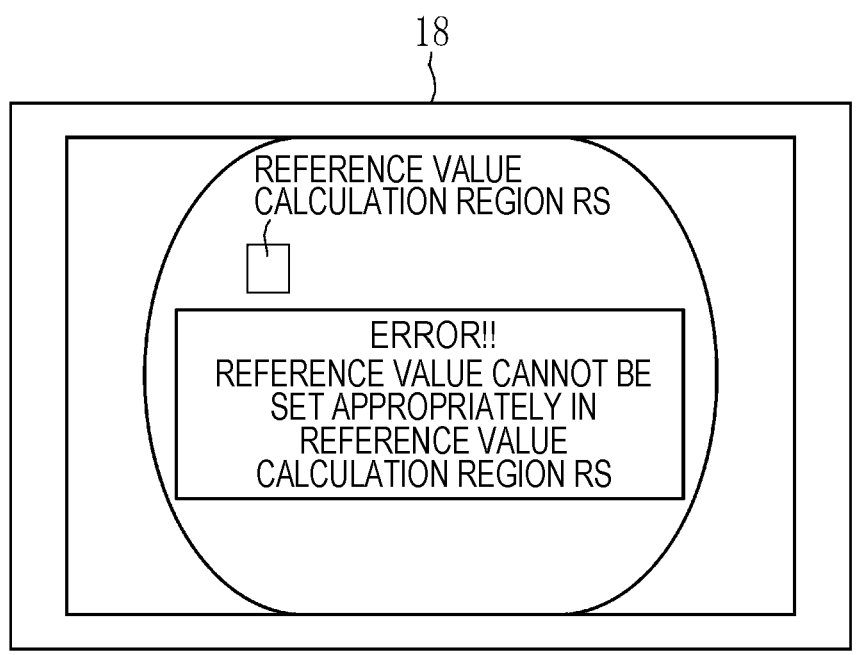
FIG. 19 is a diagram of an image illustrating error information.

On the other hand, if the representative value (e.g., average value, maximum value, or minimum value) of the reliability included in the reference value calculation region RS is less than the region determination threshold, it is determined that the reference value cannot be appropriately set in the reference value calculation region RS. In this case, the error generating unit 97 sends to the display control unit 66, error information for reporting that the reference value cannot be appropriately set in the reference value calculation region RS. As illustrated in FIG. 19, in accordance with the error information, the display control unit 66 performs control to display the error information on the monitor 18 together with the reference value calculation region RS. In accordance with this, the user resets the reference value calculation region RS by using the user interface 20.

Figure 20:
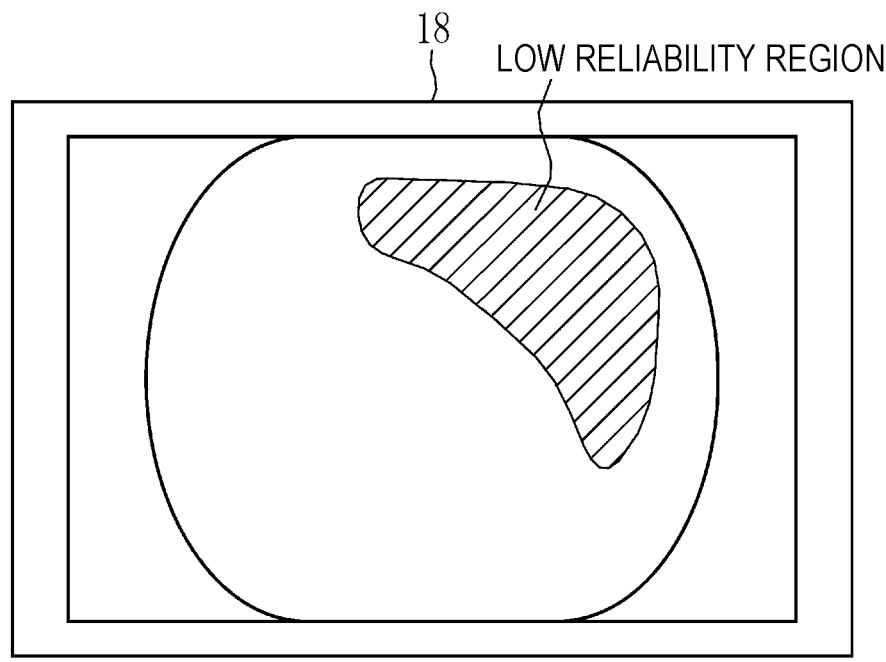
FIG. 20 is a diagram of an image illustrating a low reliability region.

If the reliability is calculated before setting the reference value calculation region RS, the region setting prohibition control unit 98 may set a low reliability region where the reliability is less than a first reliability threshold and may perform control to prohibit setting of the reference value calculation region RS for the low reliability region. If a user tries to set the reference value calculation region RS in the low reliability region, an alert indicating the prohibition of setting is preferably issued. Note that as illustrated in FIG. 20, the low reliability region is displayed to be superposed on the reference value calculation region setting image, and thus, a user can set the reference value calculation region RS avoiding the low reliability region.

Second Embodiment

In the first embodiment, the reference value calculation region RS is set in the reference value calculation region setting image, and on the basis of the oxygen saturation included in the set reference value calculation region RS, the reference value is calculated. However, in a second embodiment, the oxygen saturation in each pixel calculated by the oxygen saturation calculating unit 82 is multiplied by a weighting factor based on reliability, and addition is performed to calculate the reference value.

Figure 21:
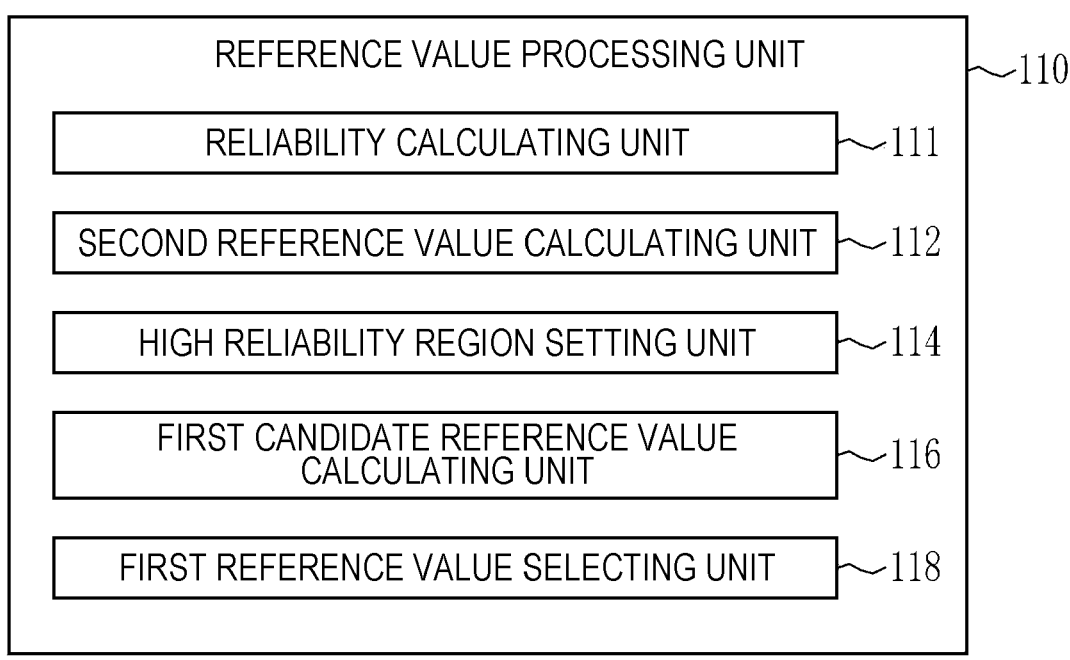
FIG. 21 is a block diagram illustrating functions of a reference value processing unit according to a second embodiment.

In the second embodiment, in place of the reference value processing unit 72 according to the first embodiment, a reference value processing unit 110 is used. The other configuration is substantially the same as the configuration according to the first embodiment. As illustrated in FIG. 21, the reference value processing unit 110 includes a reliability calculating unit 111, a second reference value calculating unit 112, a high reliability region setting unit 114, a first candidate reference value calculating unit 116, and a first reference value selecting unit 118. The reliability calculating unit 111 is the same as the reliability calculating unit 94 according to the first embodiment.

Figure 22:
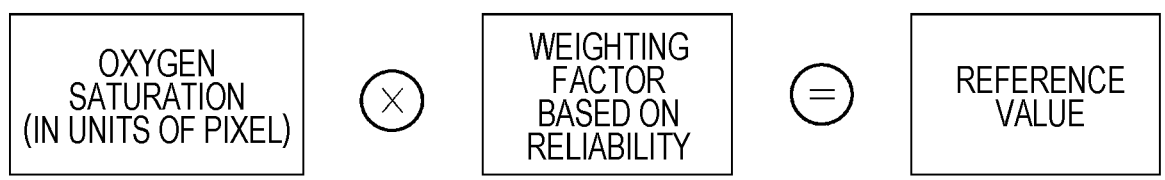
FIG. 22 illustrates a method for calculating a reference value obtained by multiplying an oxygen saturation by a weighting factor based on reliability and performing addition.

The second reference value calculating unit 112 sets a weighting factor based on reliability on the basis of reliability calculated by the reliability calculating unit 111. For example, the weighting factor may be equal to the reliability (that is, the weighting factor is set to "1" if the reliability is "1", and the weighting factor is set to "0" if the reliability is "0"). In addition, a second reliability threshold may be determined in advance as a threshold for reliability, and the weighting factor may be set to "1" if the reliability is greater than or equal to the second reliability threshold and may be set to "0" if the reliability is less than the second reliability threshold. Then, as illustrated in FIG. 22, the second reference value calculating unit 112 multiplies the oxygen saturation in each pixel calculated by the oxygen saturation calculating unit 82 by the weighting factor based on the reliability and performs addition to calculate the reference value.

Figure 23:
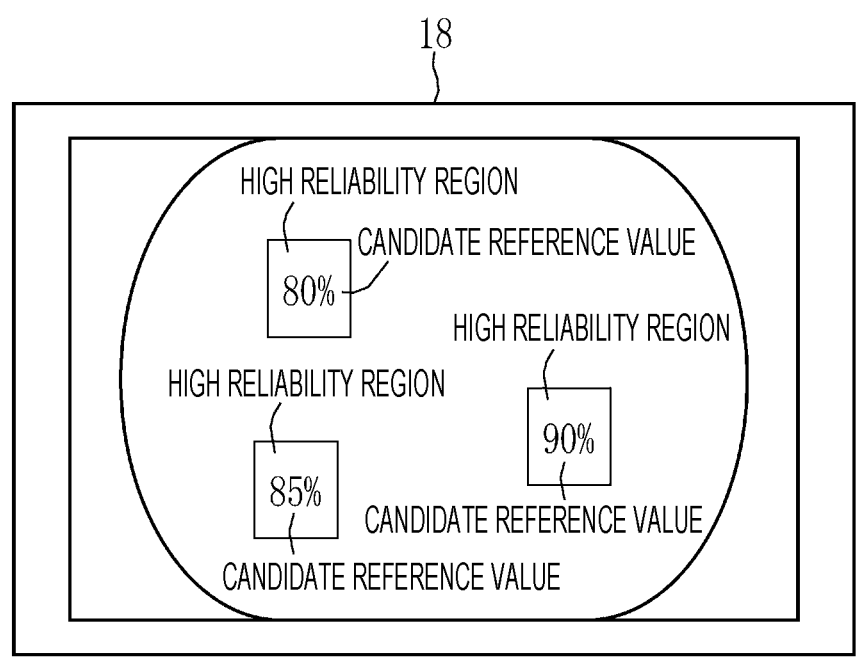
FIG. 23 is a diagram of an image illustrating high reliability regions and candidate reference values corresponding to the high reliability regions.

Note that in a case where a plurality of second reliability thresholds that are different from each other are set, the high reliability region setting unit 114 sets a plurality of high reliability regions in which the reliability is greater than or equal to each of the second reliability thresholds. In a case where the high reliability regions are set, the first candidate reference value calculating unit 116 calculates candidate reference values corresponding to the high reliability regions from the oxygen saturations included in the respective high reliability regions. The high reliability regions and the candidate reference values are sent to the display control unit 66. As illustrated in FIG. 23, the display control unit 66 performs control to display the high reliability regions and the candidate reference values on the monitor 18. In FIG. 23, in a reference value selection image (preferably the same as the reference value calculation region setting image), three high reliability regions are displayed, and the candidate reference values corresponding to the respective high reliability regions are displayed as "80%", "90%", and "85%".

Figure 24:
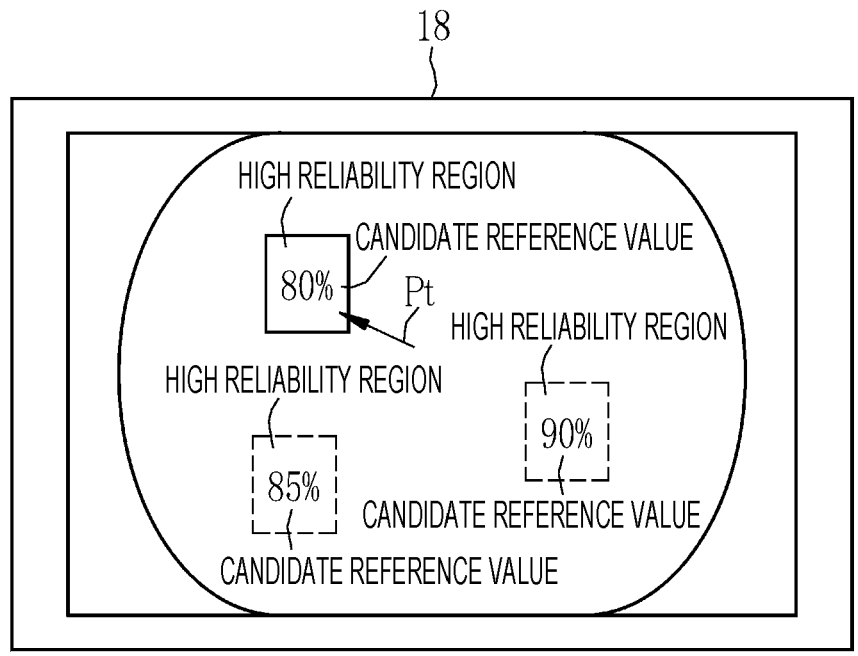
FIG. 24 illustrates a method for selecting the reference value according to the second embodiment.

From among the candidate reference values in the respective high reliability regions displayed on the monitor 18, a user selects a candidate reference value that is considered to be appropriate. The candidate reference value is selected by using the user interface 20. As illustrated in FIG. 24, in a case where the user selects, for example, the candidate reference value "80%" by operating the pointer Pt by using the user interface 20, the first reference value selecting unit 118 selects the candidate reference value "80%" as the reference value from among the three candidate reference values.

Third Embodiment

In the first embodiment, the reference value calculation region RS is set in the reference value calculation region setting image, and on the basis of the oxygen saturation included in the set reference value calculation region RS, the reference value is calculated. However, in a third embodiment, an oxygen saturation frequency distribution is calculated from oxygen saturations in the respective pixels calculated by the oxygen saturation calculating unit 82, and on the basis of the oxygen saturation frequency distribution, the reference value is calculated.

Figure 25:
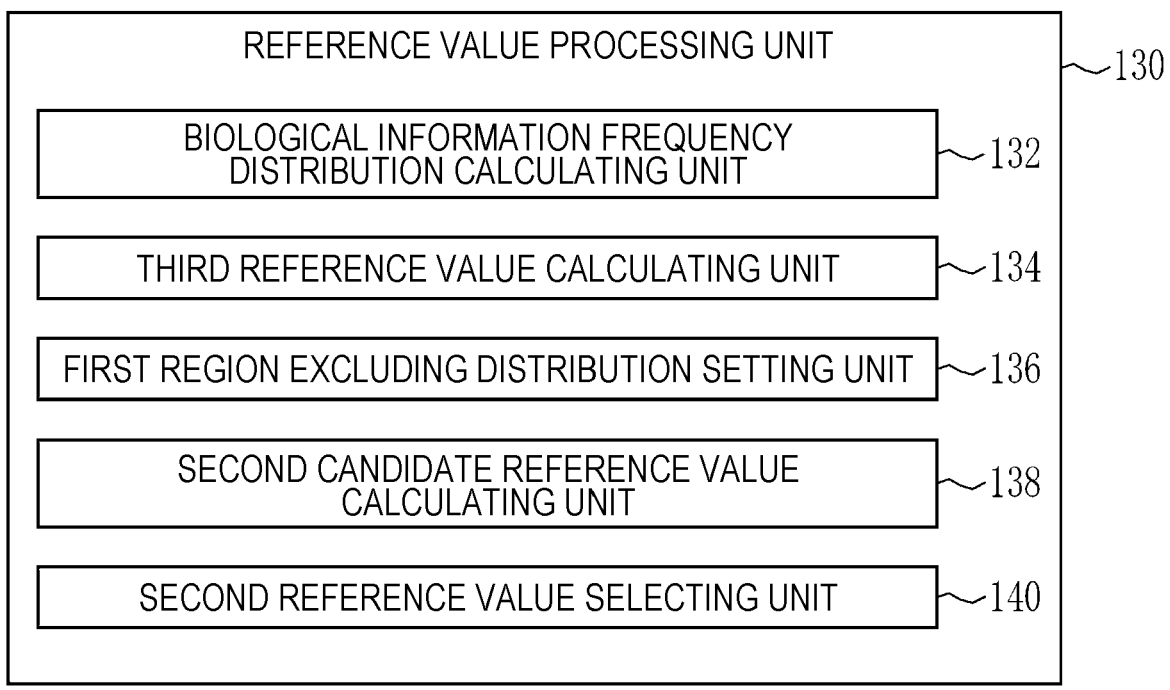
FIG. 25 is a block diagram illustrating functions of a reference value processing unit according to a third embodiment.

In the third embodiment, in place of the reference value processing unit 72 according to the first embodiment, a reference value processing unit 130 is used. The other configuration is substantially the same as the configuration according to the first embodiment. As illustrated in FIG. 25, the reference value processing unit 130 includes a biological information frequency distribution calculating unit 132, a third reference value calculating unit 134, a first region excluding distribution setting unit 136, a second candidate reference value calculating unit 138, and a second reference value selecting unit 140.

Figure 26:
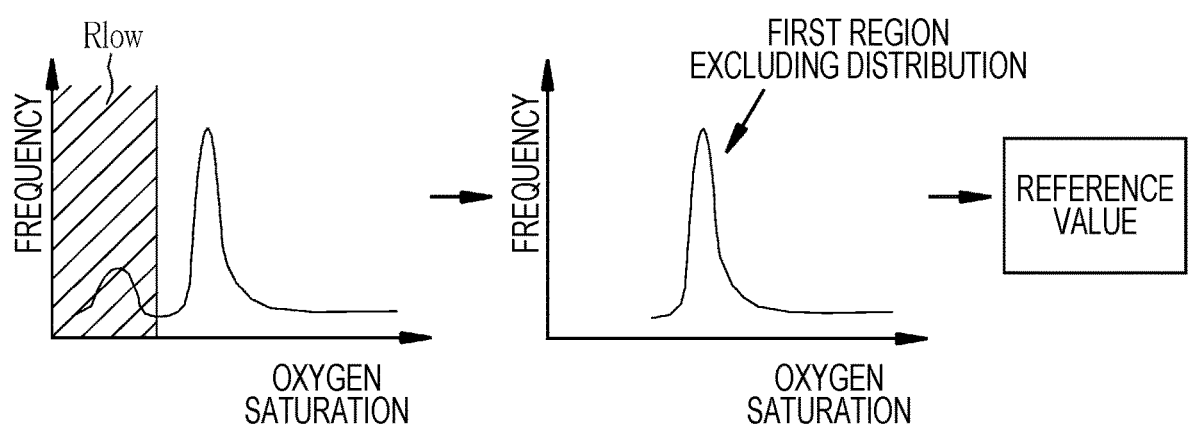
FIG. 26 illustrates a method for calculating the reference value based on an oxygen saturation frequency distribution.

As illustrated in FIG. 26, the biological information frequency distribution calculating unit 132 calculates an oxygen saturation frequency distribution from oxygen saturations in the respective pixels calculated by the oxygen saturation calculating unit 82. This oxygen saturation frequency distribution has a fixed frequency in a distribution region Rlow (a first distribution region) where the oxygen saturation is extremely low. This does not represent an actual oxygen saturation of the observation target but is considered to be based on pixel values of image signals to be used for calculating the oxygen saturation being affected by observation conditions and indicating abnormal values. Thus, it is considered that the oxygen saturation included in the distribution region Rlow has low calculation accuracy and is not an appropriate value. That is, since the oxygen saturation itself can be used as an index for measuring reliability of the oxygen saturation, in order to calculate an appropriate reference value, the first region excluding distribution setting unit 136 excludes the distribution in the region Rlow from the oxygen saturation frequency distribution to obtain a first region excluding distribution. Then, the third reference value calculating unit 134 obtains a representative value (e.g., average value, maximum value, or minimum value) of the oxygen saturations included in the first region excluding distribution to calculate the reference value. Note that the region to be excluded from the oxygen saturation frequency distribution may be, in addition to the distribution region Rlow, a distribution region Rhigh (the first distribution region) where the oxygen saturation is extremely high.

Figure 27:
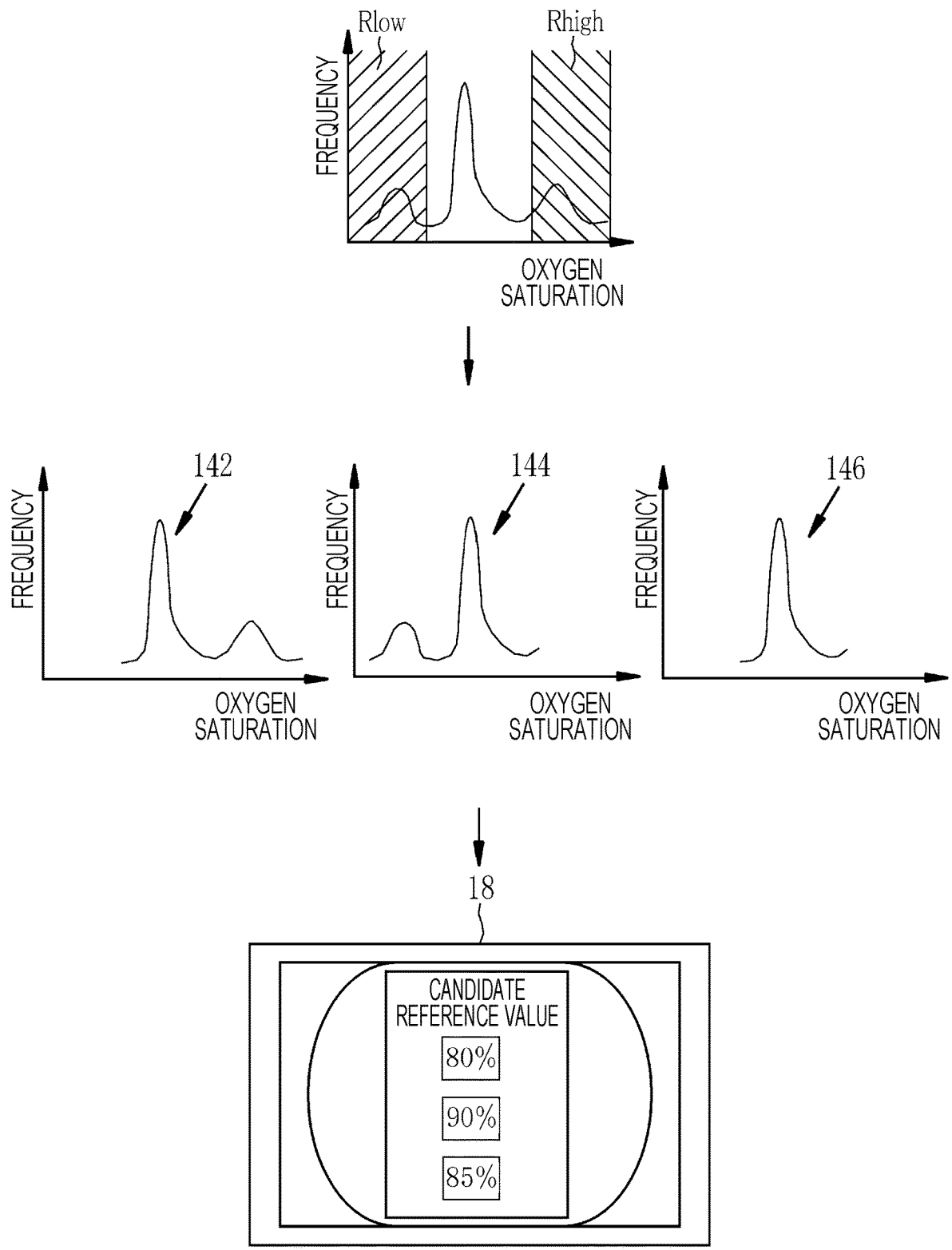
FIG. 27 illustrates a method for calculating the reference value based on a plurality of first region excluding distributions.

Note that in a case where a plurality of distribution regions are to be excluded, as illustrated in FIG. 27, the first region excluding distribution setting unit 136 sets a plurality of first region excluding distributions excluding the distribution regions. In FIG. 27, a first region excluding distribution 142 excluding only the distribution region Rlow from the oxygen saturation frequency distribution, a first region excluding distribution 144 excluding only the distribution region Rhigh from the oxygen saturation frequency distribution, and a first region excluding distribution 146 excluding the distribution region Rlow and the distribution region Rhigh from the oxygen saturation frequency distribution are set. Then, the second candidate reference value calculating unit 138 calculates candidate reference values from the oxygen saturations included in the respective first region excluding distributions 142, 144, and 146. The plurality of calculated candidate reference values are sent to the display control unit 66. The display control unit 66 displays the plurality of candidate reference values on the monitor 18 in a reference value selection image. In this example, as the candidate reference values, "80%", "90%", and "85%" are displayed.

Figure 28:
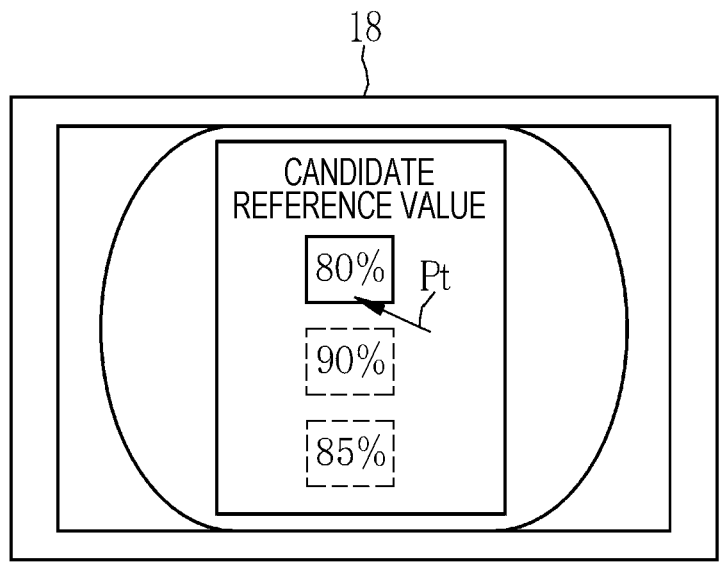
FIG. 28 illustrates a method for selecting the reference value according to a third embodiment.

From among the candidate reference values displayed on the monitor 18, a user selects a candidate reference value that is considered to be appropriate. The candidate reference value is selected by using the user interface 20. As illustrated in FIG. 28, in a case where the user selects, for example, the candidate reference value "80%" by operating the pointer Pt by using the user interface 20, the second reference value selecting unit 140 selects the candidate reference value "80%" as the reference value from among the three candidate reference values.

Fourth Embodiment

In the first embodiment, the reference value calculation region RS is set in the reference value calculation region setting image, and on the basis of the oxygen saturation included in the set reference value calculation region RS, the reference value is calculated. However, in a fourth embodiment, an oxygen saturation frequency distribution is calculated from a signal ratio (an arithmetic value) to be used for calculating the oxygen saturation, and from the oxygen saturation frequency distribution, the reference value is calculated. Note that the signal ratio is obtained through arithmetic processing between different image signals (e.g., the B1 image signal and the G2 image signal, or the G2 image signal and the R2 image signal), and thus corresponds to an arithmetic value.

Figure 29:
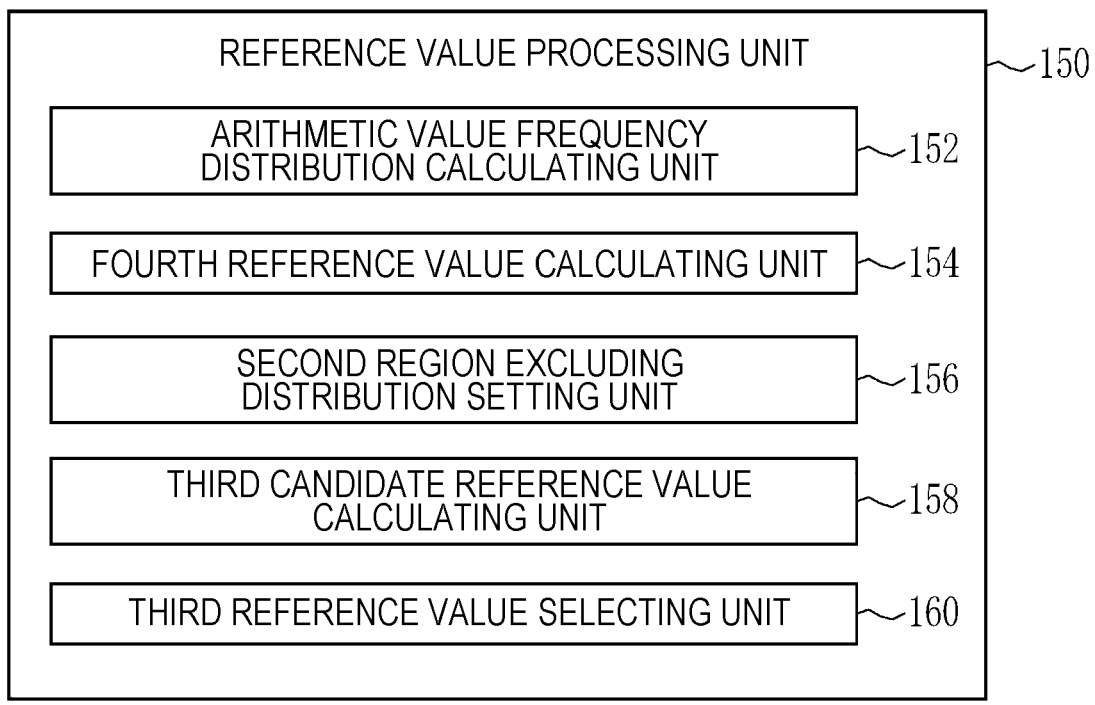
FIG. 29 is a block diagram illustrating functions of a reference value processing unit according to a fourth embodiment.

In the fourth embodiment, in place of the reference value processing unit 72 according to the first embodiment, a reference value processing unit 150 is used. The other configuration is substantially the same as the configuration according to the first embodiment. As illustrated in FIG. 29, the reference value processing unit 150 includes an arithmetic value frequency distribution calculating unit 152, a fourth reference value calculating unit 154, a second region excluding distribution setting unit 156, a third candidate reference value calculating unit 158, and a third reference value selecting unit 160.

Figure 30:
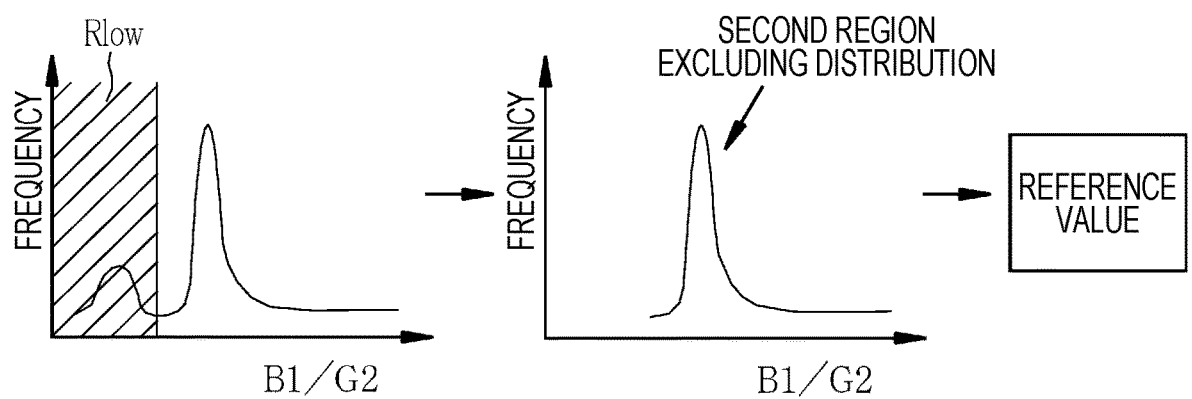
FIG. 30 illustrates a method for calculating the reference value based on a signal ratio B1/G2 frequency distribution.

As illustrated in FIG. 30, the arithmetic value frequency distribution calculating unit 152 calculates, from a signal ratio obtained by the signal ratio calculating unit 78, B1/G2 for example, a frequency distribution of the signal ratio B1/G2. The frequency distribution of the signal ratio B1/G2 has a fixed frequency in a distribution region Rlow where the signal ratio B1/G2 is extremely low. This is considered to be based on pixel values of image signals to be used for calculating the oxygen saturation being affected by observation conditions and indicating abnormal values. Thus, it is considered that the signal ratio B1/G2 included in the distribution region Rlow has low calculation accuracy for the oxygen saturation and is not an appropriate value. Note that the arithmetic value frequency distribution calculating unit 152 may calculate a frequency distribution of the signal ratio R2/G2 in place of or in addition to the signal ratio B1/G2.

Thus, the signal ratio B1/G2 can be used as an index for measuring reliability of the oxygen saturation. Accordingly, in a case where the signal ratio B1/G2 is a specific signal ratio (a specific arithmetic value) used for calculating a low-reliability oxygen saturation, the second region excluding distribution setting unit 156 excludes the distribution in the distribution region Rlow, which is one of second distribution regions having the specific signal ratio, from the signal ratio B1/G2 frequency distribution to obtain a second region excluding distribution. Then, the fourth reference value calculating unit 154 obtains a representative value (e.g., average value, maximum value, or minimum value) of the signal ratio B1/G2 included in the second region excluding distribution. On the basis of the representative value of the signal ratio B1/G2 and the signal ratio R2/G2, the oxygen saturation calculating unit 82 calculates an oxygen saturation. The calculated oxygen saturation is calculated as the reference value. Note that the second distribution region may be, in addition to the distribution region Rlow, a distribution region Rhigh where the signal ratio B1/G2 is extremely high.

Figure 31:
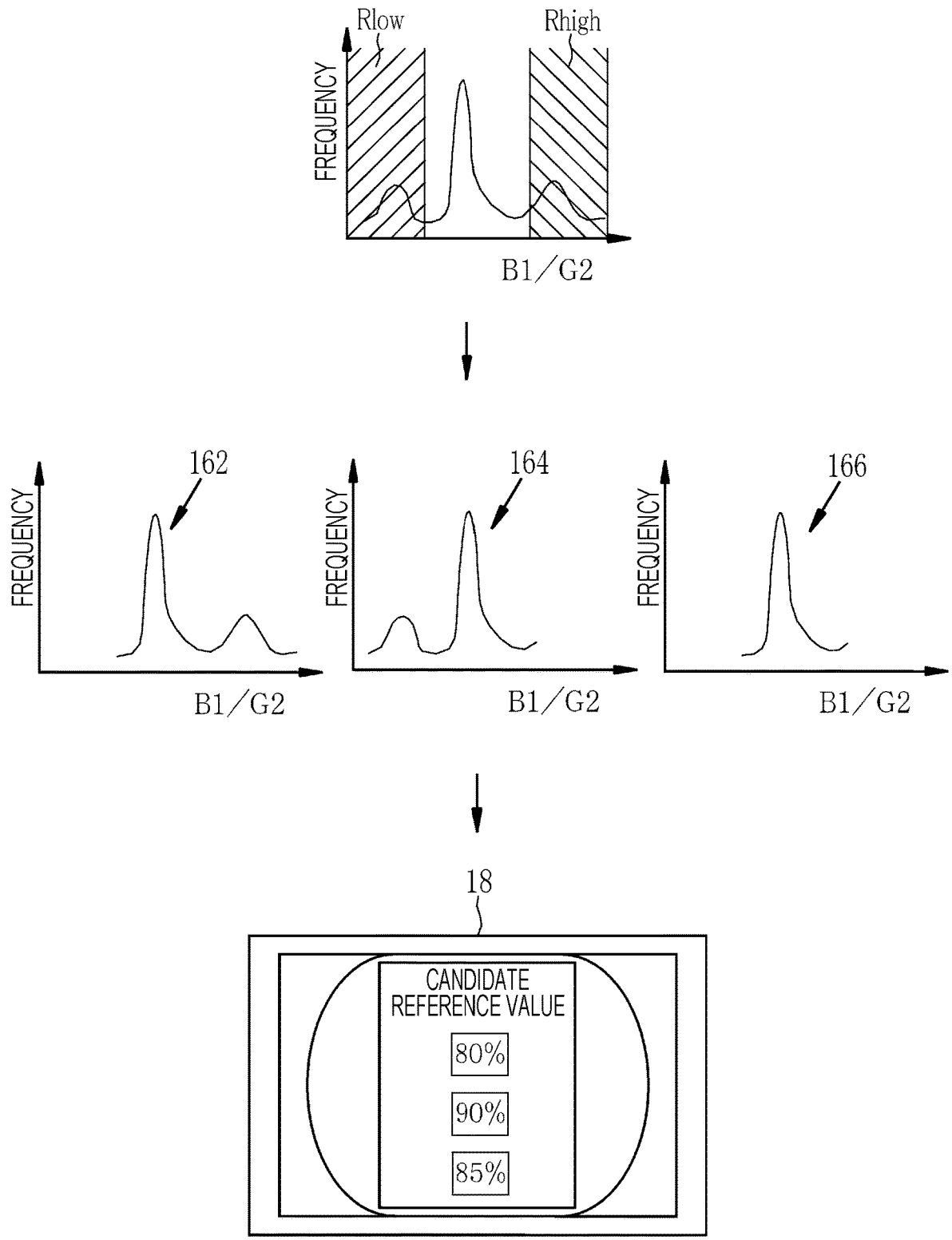
FIG. 31 illustrates a method for calculating the reference value based on a plurality of second region excluding distributions.

Note that in a case where a plurality of distribution regions are to be excluded, as illustrated in FIG. 31, the second region excluding distribution setting unit 156 sets a plurality of second region excluding distributions excluding the distribution regions. In FIG. 31, a second region excluding distribution 162 excluding only the distribution region Rlow from the signal ratio B1/G2 frequency distribution, a second region excluding distribution 164 excluding only the distribution region Rhigh from the signal ratio B1/G2 frequency distribution, and a second region excluding distribution 166 excluding the distribution region Rlow and the distribution region Rhigh from the signal ratio B1/G2 frequency distribution are set. Then, the third candidate reference value calculating unit 158 calculates oxygen saturations from representative values of the signal ratio B1/G2 included in the respective second region excluding distributions 162, 164, and 166. The oxygen saturations corresponding to the second region excluding distributions 162, 164, and 166 are calculated as candidate reference values. The plurality of calculated candidate reference values are sent to the display control unit 66. The display control unit 66 displays the plurality of candidate reference values on the monitor 18 in a reference value selection image. In this example, as the candidate reference values, "80%", "90%", and "85%" are displayed.

From among the candidate reference values displayed on the monitor 18, a user selects a candidate reference value that is considered to be appropriate. The candidate reference value is selected by using the user interface 20. In a case where the user selects, for example, the candidate reference value "80%" by operating the pointer Pt by using the user interface 20, the third reference value selecting unit 160 selects the candidate reference value "80%" as the reference value from among the three candidate reference values (see FIG. 28).

Note that although the signal ratio B1/G2 frequency distribution is calculated as the signal ratio frequency distribution in the fourth embodiment, a frequency distribution of a signal ratio B1/(a×B2+b×G2) where the denominator and the numerator have the same wavelength component may be calculated. Since the denominator and the numerator have different wavelength components in the signal ratio B1/G2, the oxygen saturation may not be calculated appropriately. Accordingly, in the signal ratio B1/(a×B2+b×G2) (a and b are weighting factors for the denominator), the B1 image signal is used as it is as the numerator, and a value obtained by weighting the "B2 image signal" having a short wavelength component and adding it to the G2 image signal is used as the denominator. Thus, the denominator and the numerator can have the same wavelength component. This enables calculation of the oxygen saturation appropriately.

Fifth Embodiment

In the first embodiment, the reference value calculation region RS is set in the reference value calculation region setting image, and on the basis of the oxygen saturation included in the set reference value calculation region RS, the reference value is calculated. However, in a fifth embodiment, a user can set the reference value as appropriate.

Figure 32:
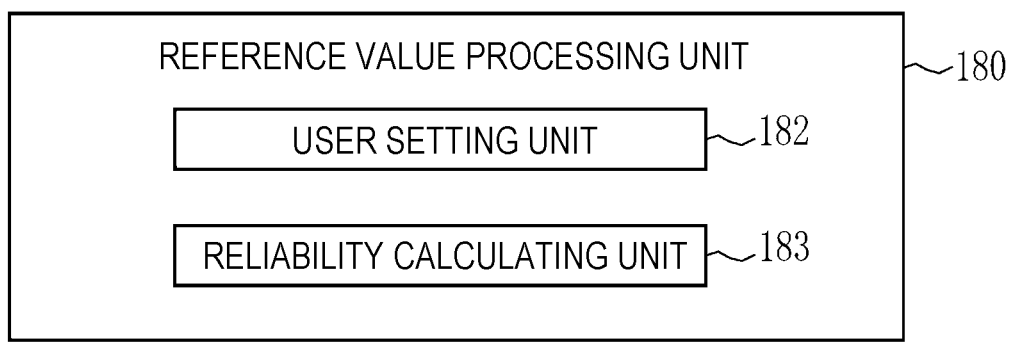
FIG. 32 is a block diagram illustrating functions of a reference value processing unit according to a fifth embodiment.
Figure 33:
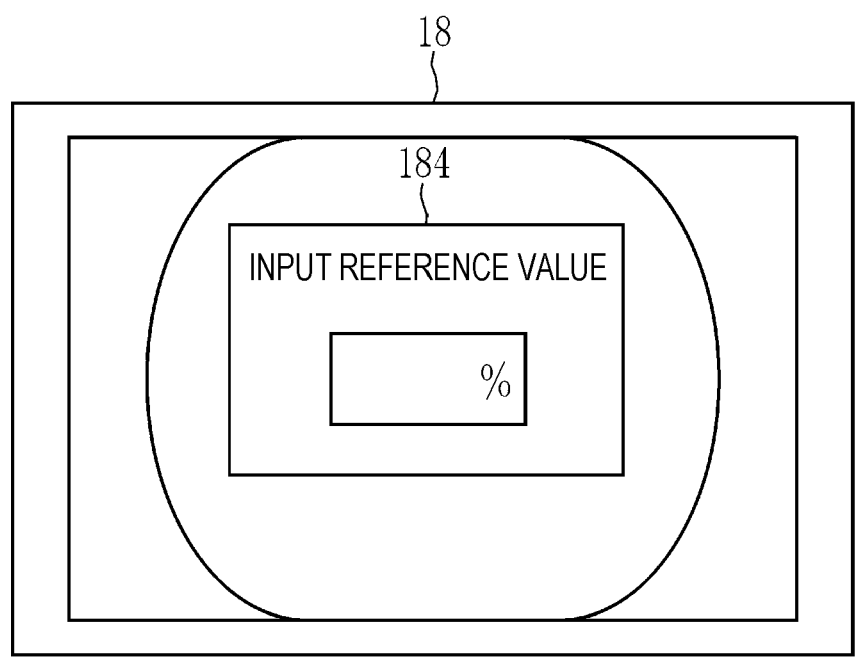
FIG. 33 is a diagram of an image illustrating a reference value input screen for directly inputting a numeric value for setting the reference value.

In the fifth embodiment, in place of the reference value processing unit 72 according to the first embodiment, a reference value processing unit 180 is used. As illustrated in FIG. 32, the reference value processing unit 180 is provided with a user setting unit 182. In a case where a reference value user setting mode is set by using the user interface 20, as illustrated in FIG. 33, the display control unit 66 performs control to display a reference value input screen 184 for inputting a reference value on the monitor 18. A user inputs a numeric value (e.g., the oxygen saturation "80%") on the input screen by using the user interface 20. When a specific time elapses after the input of the numeric value, the user setting unit 182 sets the input numeric value as the reference value. The set reference value is adjusted as appropriate by using reliability calculated by a reliability calculating unit 183, which will be described later. If the reliability is normal, the set reference value is used as it is; if the reliability is abnormal, the set reference value is adjusted in accordance with the reliability.

The reliability calculating unit 183 calculates an average pixel value of the B1 image signal, the G2 image signal, and the R2 image signal to be used for calculating the oxygen saturation, and calculates the reliability in accordance with the average pixel value. In a case where all of the B1 image signal, the G2 image signal, and the R2 image signal fall within an appropriate pixel value range, the reliability is preferably set as normal. In contrast, in a case where any of the B1 image signal, the G2 image signal, and the R2 image signal falls out of the appropriate pixel value range, the reliability is set as abnormal. If the reliability is abnormal, the set reference value is multiplied by a correction factor for setting normal reliability, and the reference value is adjusted.

Figure 34:
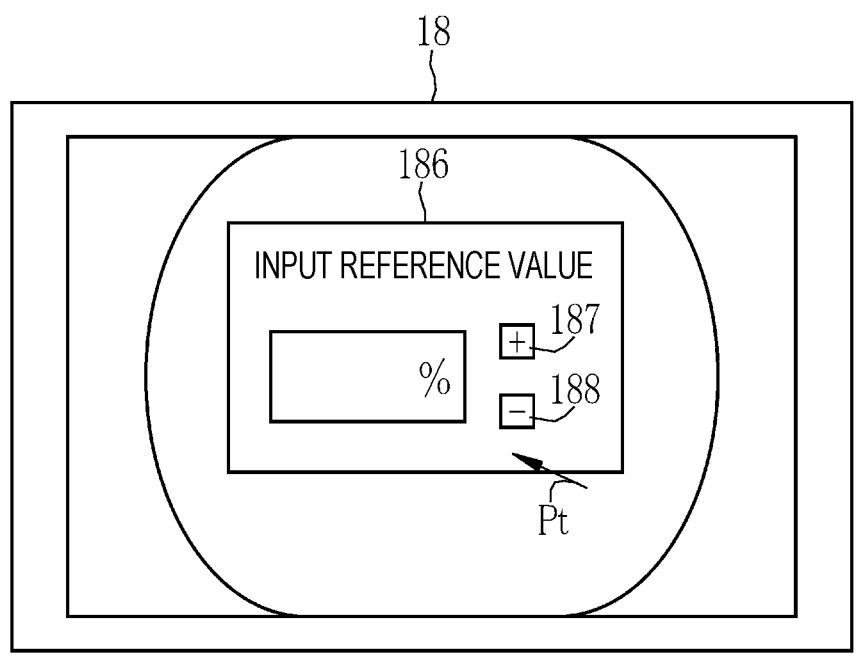
FIG. 34 is a diagram of an image illustrating a reference value input screen for increasing or decreasing a numeric value for setting the reference value stepwise.

Note that, in place of the reference value input screen 184 for inputting the numeric value itself, as illustrated in FIG. 34, a reference value input screen 186 for increasing or decreasing the numeric value stepwise may be used. The reference value input screen 186 is provided with a "+" button 187 for increasing the numeric value in units of a specific numeric value and a "−" button 188 for decreasing the numeric value in units of the specific numeric value. A user operates the "+" button 187 and the "−" button 188 with the movable pointer Pt by using the user interface 20, thereby setting a specific value. When a specific time elapses after the setting of the specific value, the user setting unit 182 confirms the set specific value as the reference value.

Figure 35:
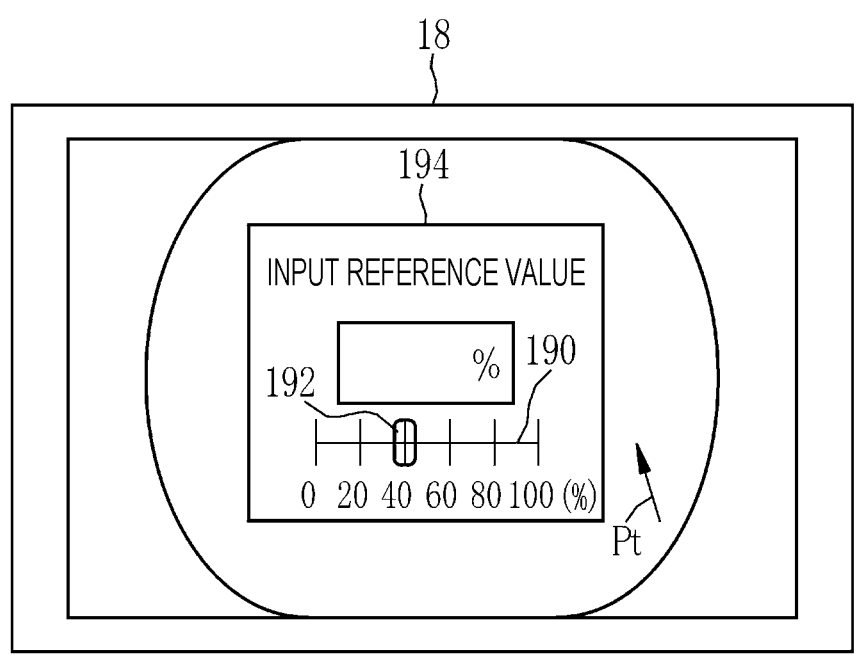
FIG. 35 is a diagram of an image illustrating a reference value input screen for increasing or decreasing a numeric value for setting the reference value stepwise by using a slide bar and a slider.

As a method for increasing or decreasing the numeric value stepwise, in addition to using the reference value input screen 186, as illustrated in FIG. 35, a reference value input screen 194 may be used. The reference value input screen 194 is provided with a slide bar 190 on which numeric values from "0%" to "100%" are allocated and a slider 192 that is movable on the slide bar. A user moves the slider 192 with the movable pointer Pt by using the user interface 20 to a part where a numeric value desired to be set is allocated on the slide bar 190. When a specific time elapses after the setting of the slider 192 to the part of the numeric value desired to be set, the user setting unit 182 confirms the numeric value at the part where the slider 192 is located on the slide bar 190 as the reference value.

Note that as a method for setting the reference value by a user, a reference value setting button (not illustrated) is provided for the operating unit of the endoscope, and each time a pressing operation is performed on the reference value setting button, the reference value is increased or decreased by a specific value. In this case, by performing a press-and-hold operation on the reference value setting button, the reference value may be continuously increased or decreased.

Figure 36:
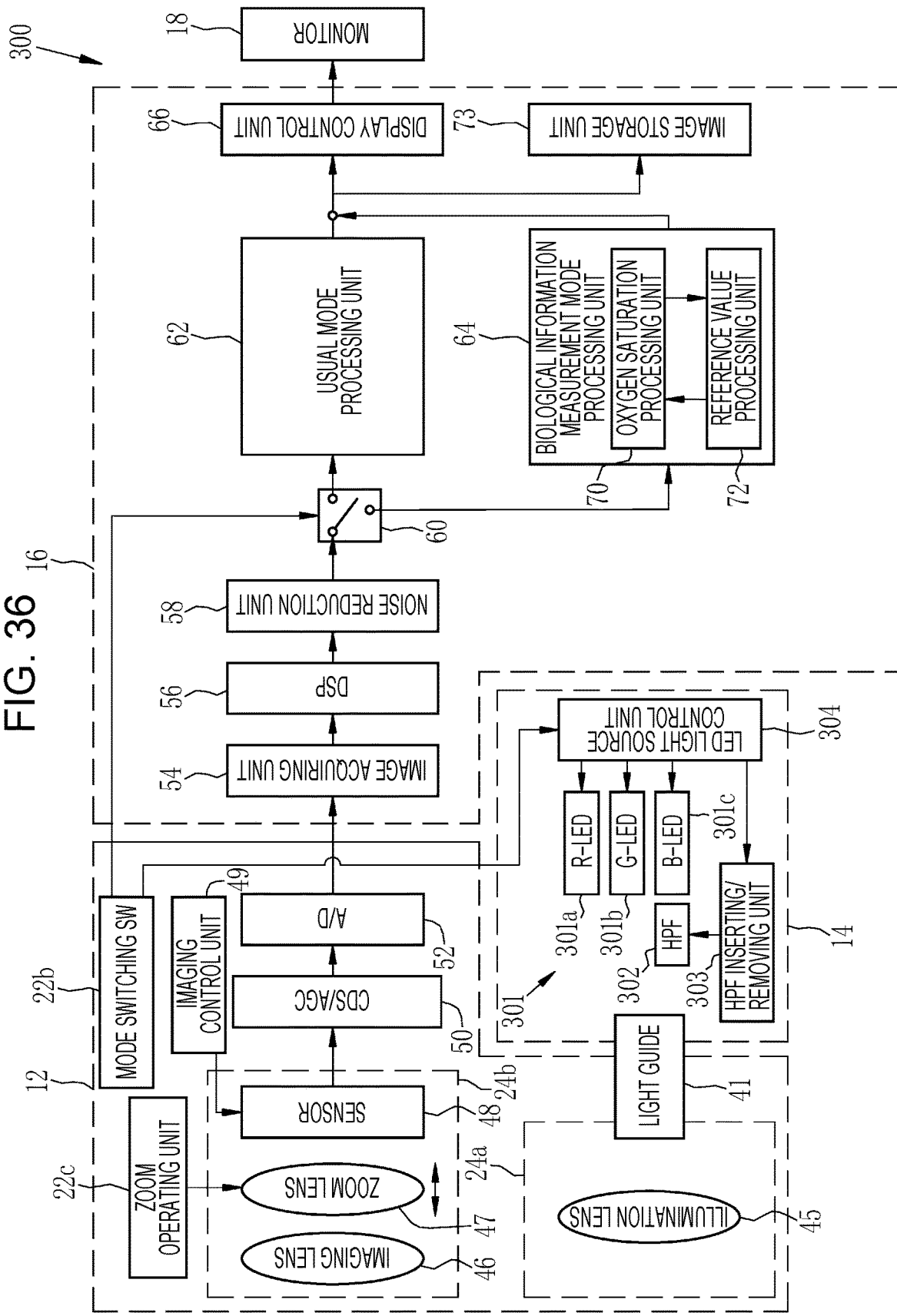
FIG. 36 is a block diagram of an endoscope system including a light source device having a plurality of light emitting diodes (LEDs)

Note that in the above embodiments, a light source device different from the light source device 14 may also be used. In the light source device 14 of an endoscope system 300, in place of the first and second blue laser light sources 34 and 36 and the light source control unit 40, as illustrated in FIG. 36, a light emitting diode (LED) light source unit 301 and a LED light source control unit 304 are provided. In addition, the fluorescent body 44 is not provided in the illumination optical system 24a of the endoscope system 300. The other configuration is substantially the same as the configuration of the endoscope system 10 according to the first embodiment.

Figure 37:
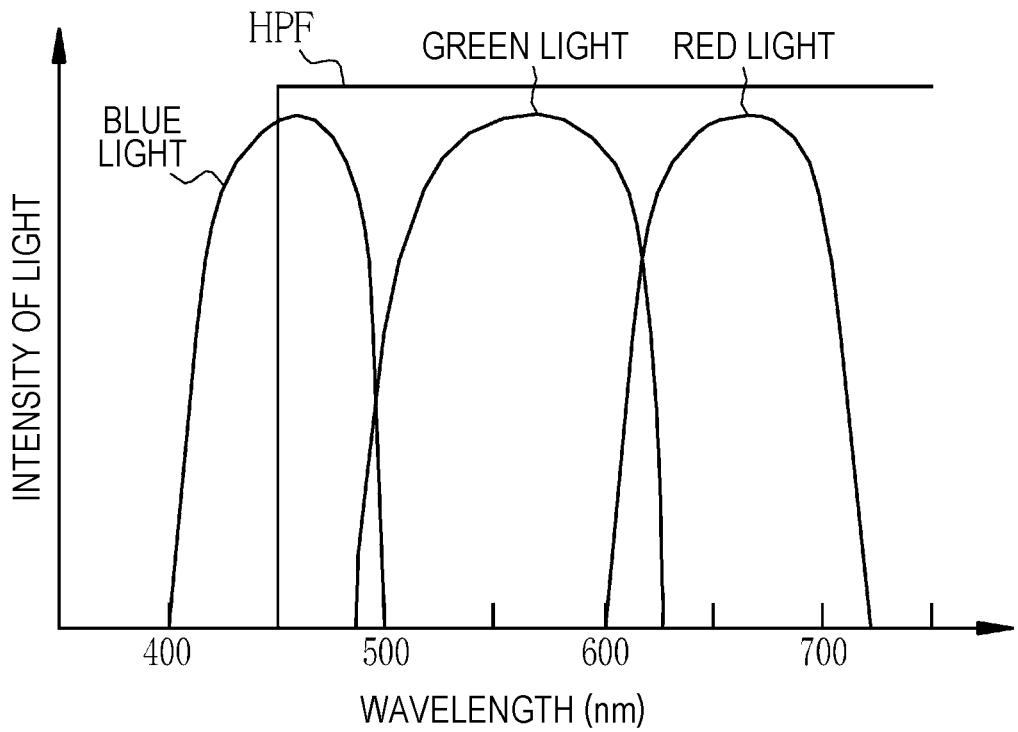
FIG. 37 is a graph illustrating light emission bands of the LEDs and characteristics of a high-pass filter (HPF)

The LED light source unit 301 has a R-LED 301a, a G-LED 301b, and a B-LED 301c as light sources that emit light restricted to specific wavelength bands. As illustrated in FIG. 37, the R-LED 301a emits light of a red range, in a red region of 600 to 720 nm (hereinafter simply referred to as red light), and the G-LED 301b emits light of a green range, in a green region of 480 to 620 nm (hereinafter simply referred to as green light). In addition, the B-LED 301c emits light of a blue range, in a blue region of 400 to 500 nm (hereinafter simply referred to as blue light).

The LED light source unit 301 further has a high-pass filter (HPF) 302 inserted/removed into/from an optical path of blue light emitted from the B-LED 301c. The high-pass filter 302 cuts blue light in the wavelength band of less than or equal to 450 nm and transmits light in the wavelength band of longer than 450 nm.

At the cut-off wavelength (450 nm) of the high-pass filter 302, the absorption coefficient of oxidized hemoglobin and the absorption coefficient of reduced hemoglobin are substantially equal to each other (see FIG. 10), and from this wavelength, the magnitude relation between the absorption coefficient of oxidized hemoglobin and the absorption coefficient of reduced hemoglobin is reversed. In the above embodiment, since the correlations stored in the correlation storage unit 80 are of a case where the absorption coefficient of oxidized hemoglobin is larger than the absorption coefficient of reduced hemoglobin, in a signal based on a wavelength band of less than or equal to the cut-off wavelength, the signal ratio B1/G2 is decreased from an original value measured at 473 nm, and as a result, an inaccurate oxygen saturation is calculated. Thus, when the B1 image signal for calculating the oxygen saturation is acquired, the high-pass filter 302 prevents the observation target from being irradiated with light at the wavelength band of less than or equal to the cut-off wavelength.

Thus, the high-pass filter 302 is inserted before the B-LED 301c in the biological information measurement mode and is removed to a removal position in the usual observation mode. The high-pass filter 302 is inserted/removed by an HPF inserting/removing unit 303 under control of the LED light source control unit 304.

Figure 38:
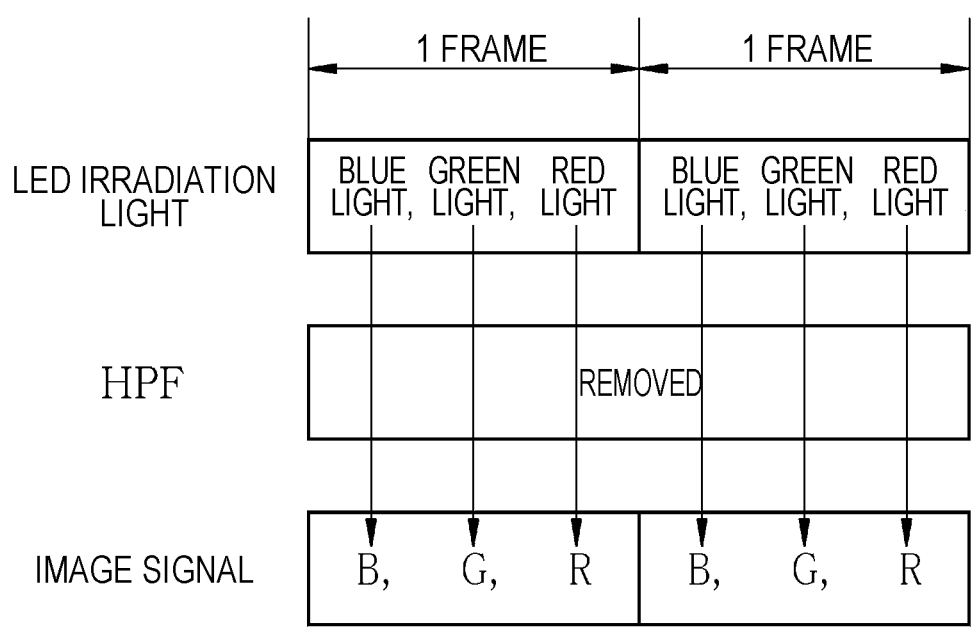
FIG. 38 illustrates imaging control in the usual observation mode in a case where the light source device having the plurality of LEDs is used.

The LED light source control unit 304 controls turning on/off of each of the LEDs 301a to 301c of the LED light source unit 301 and insertion/removal of the high-pass filter 302. Specifically, as illustrated in FIG. 38, in the usual observation mode, the LED light source control unit 304 turns on all of the LEDs 301a to 301c and removes the high-pass filter 302 from the optical path of the B-LED 301c.

Figure 39:
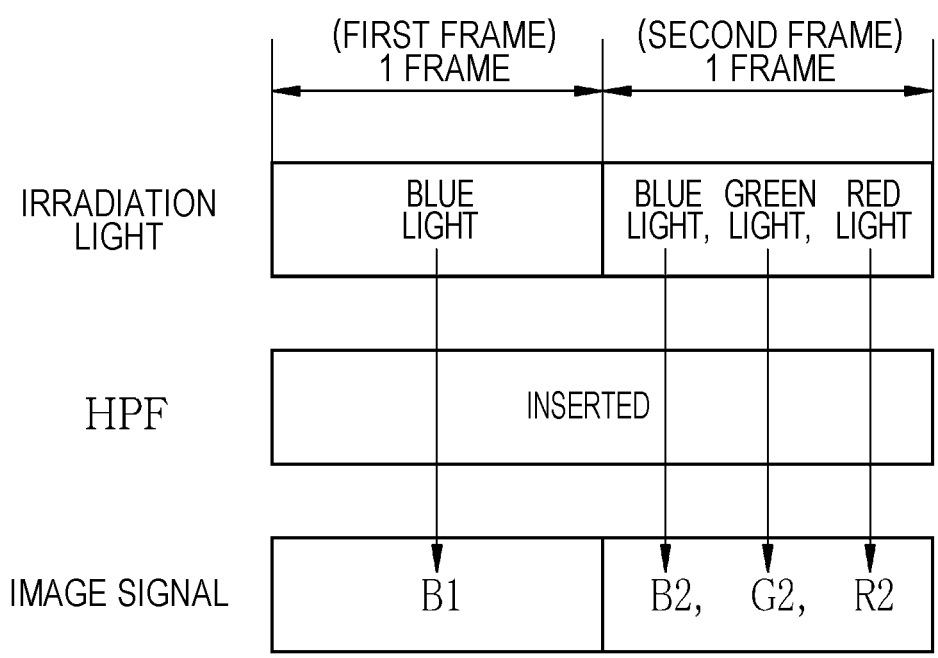
FIG. 39 illustrates imaging control in the biological information measurement mode in a case where the light source device having the plurality of LEDs is used.

On the other hand, as illustrated in FIG. 39, in the biological information measurement mode, the LED light source control unit 304 inserts the high-pass filter 302 into the optical path of the B-LED 301c. In a first frame, the B-LED 301c is turned on, and the R-LED 301a and the G-LED 301b are turned off, so that the observation target is irradiated with blue light from which the wavelength band of less than or equal to 450 nm is cut. In a second frame, all of the R-LED 301a, the G-LED 301b, and the B-LED 301c are turned on, so that the observation target is irradiated with white light formed of blue light from which the wavelength band of less than or equal to 450 nm is cut in the blue light emitted by the B-LED 301c, the red light emitted by the R-LED 301a, and the green light emitted by the G-LED 301b. Thus, the sensor 48 outputs the B1 image signal in the first frame, and outputs the R2 image signal, the G2 image signal, and the B2 image signal in the second frame. Accordingly, subsequent processing can be performed as in the endoscope system 10 according to the first embodiment.

Note that the observation target is imaged with the high-pass filter 302 inserted in both the first frame and the second frame in the biological information measurement mode in the above embodiment; however, the high-pass filter 302 may be inserted only in the first frame and may be removed in the second frame. In addition, in the first frame in the biological information measurement mode, only the B-LED 301c is turned on, and the observation target is irradiated with only the blue light; however, also in the first frame, the R-LED 301a and the G-LED 301b may be turned on, and the sensor 48 may output the R1 image signal and the G1 image signal.

Figure 40:
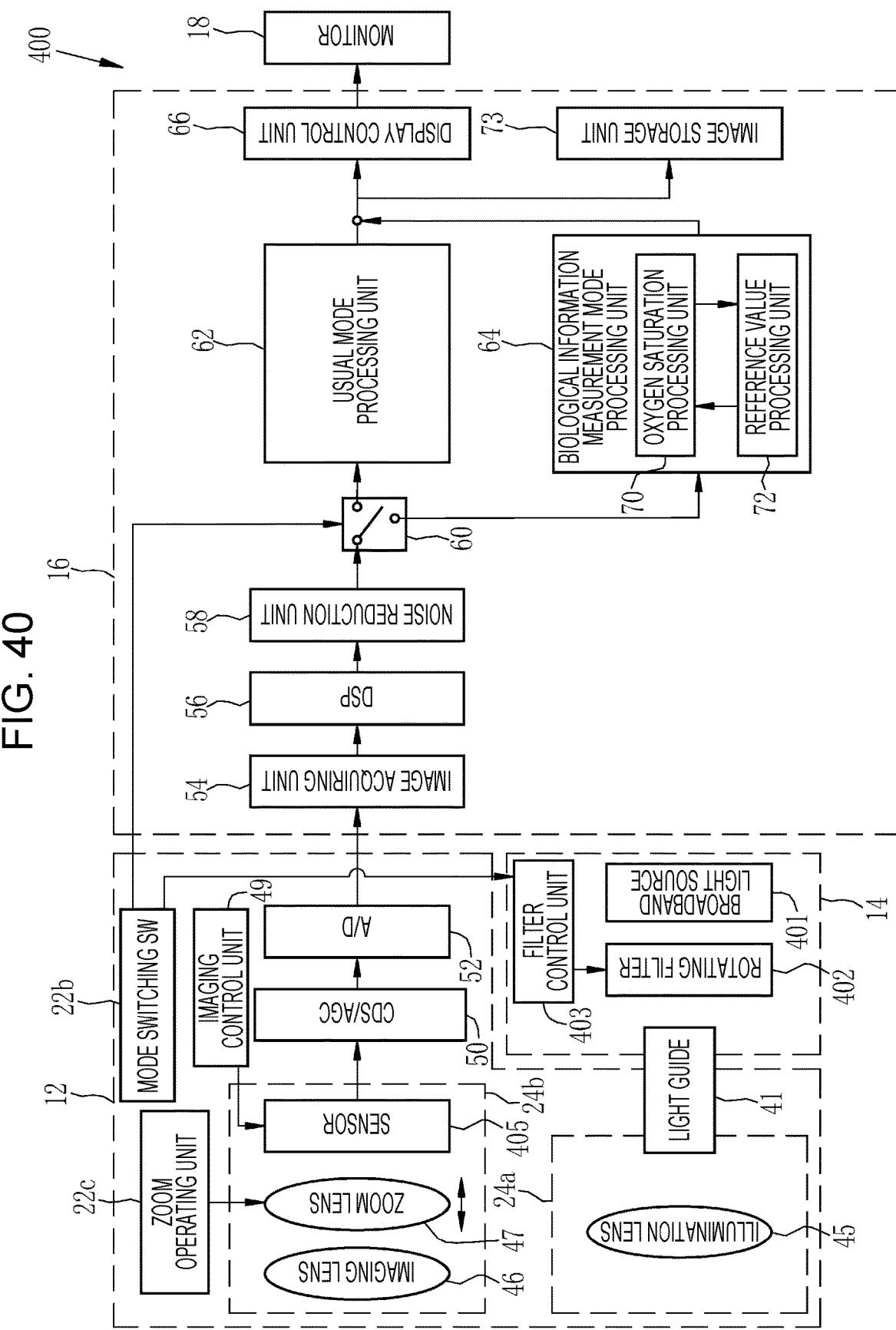
FIG. 40 is a block diagram of an endoscope system including a light source device having a rotating filter.

As illustrated in FIG. 40, in the light source device 14 of an endoscope system 400, in place of the first and second blue laser light sources 34 and 36 and the light source control unit 40, a broadband light source 401, a rotating filter 402, and a rotating filter control unit 403 are provided. In addition, a sensor 405 of the endoscope system 400 is a monochrome imaging element without a color filter. The other configuration is substantially the same as the configuration of the endoscope system 10 according to the first embodiment.

The broadband light source 401 is constituted by, for example, a xenon lamp, a white LED, or the like and emits white light whose wavelength range is from blue to red. The rotating filter 402 includes a usual observation mode filter 410 and a biological information measurement mode filter 411 (see FIG. 41), and is movable in the diameter direction between a first position and a second position on an optical path on which white light emitted from the broadband light source 401 enters the light guide 41. The first position is for the usual observation mode for arranging the usual observation mode filter 410, and the second position is for the biological information measurement mode for arranging the biological information measurement mode filter 411. The mutual movement of the rotating filter 402 to the first position and the second position is controlled by the rotating filter control unit 403 in accordance with the selected observation mode. In addition, the rotating filter 402 rotates in accordance with the imaging frame of the sensor 405 in a state of being arranged at the first position or the second position. The rotation speed of the rotating filter 402 is controlled by the rotating filter control unit 403 in accordance with the selected observation mode.

Figure 41:
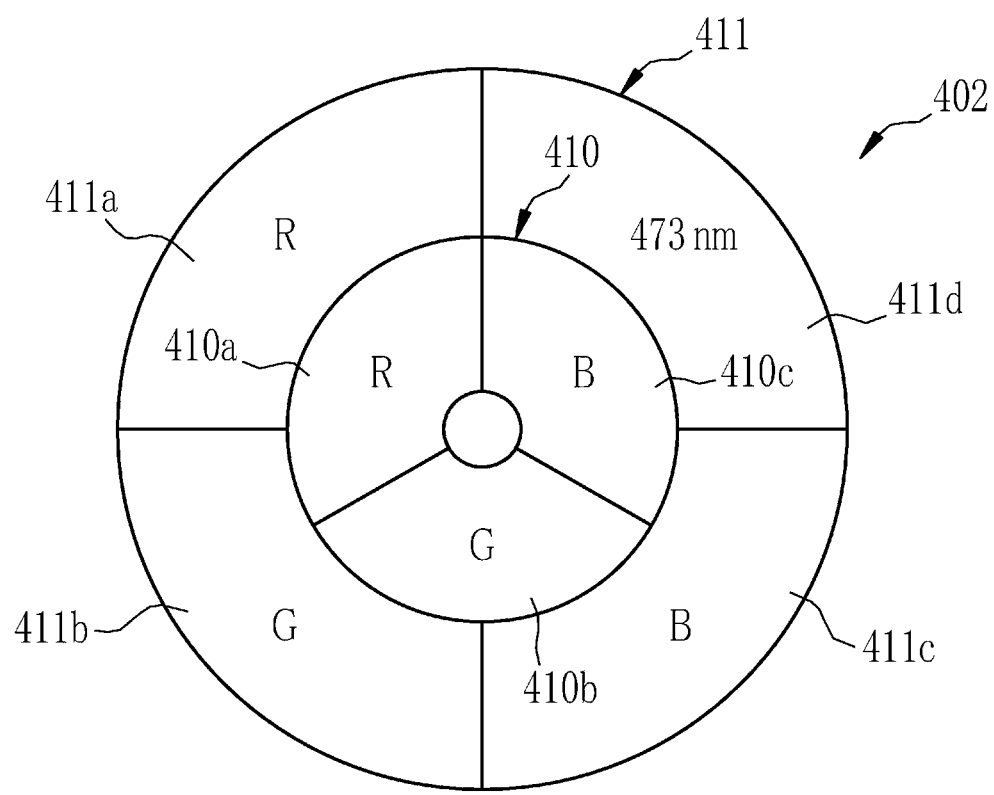
FIG. 41 is a plan view of the rotating filter.

As illustrated in FIG. 41, the usual observation mode filter 410 is provided on an inner periphery of the rotating filter 402. The usual observation mode filter 410 has a R filter 410a that transmits red light, a G filter 410b that transmits green light, and a B filter 410c that transmits blue light. Thus, when the rotating filter 402 is arranged at the first position for the usual observation mode, white light from the broadband light source 401 enters any of the R filter 410a, the G filter 410b, and the B filter 410c in accordance with the rotation of the rotating filter 402. Accordingly, the observation target is sequentially irradiated with red light, green light, and blue light in accordance with the filter through which the light passes, and the sensor 405 images the observation target by using individual reflected light to sequentially output a R image signal, a G image signal, and a B image signal.

In addition, the biological information measurement mode filter 411 is provided on an outer periphery of the rotating filter 402. The biological information measurement mode filter 411 has a R filter 411a that transmits red light, a G filter 411b that transmits green light, a B filter 411c that transmits blue light, and a narrowband filter 411d that transmits barrow band light of 473±10 nm. Thus, when the rotating filter 402 is arranged at the second position for the biological information measurement mode, white light from the broadband light source 401 enters any of the R filter 411a, the G filter 411b, the B filter 411c, and the narrowband filter 411d in accordance with the rotation of the rotating filter 402. Accordingly, the observation target is sequentially irradiated with red light, green light, blue light, and the narrowband light (473 nm) in accordance with the filter through which the light passes, and the sensor 405 images the observation target by using individual reflected light to sequentially output a R image signal, a G image signal, a B image signal, and a narrowband image signal.

The R image signal and the G image signal obtained in the biological information measurement mode correspond to the R1 (or R2) image signal and the G1 (or G2) image signal according to the first embodiment. In addition, the B image signal obtained in the biological information measurement mode corresponds to the B2 image signal according to the first embodiment, and the narrowband image signal corresponds to the B1 image signal. Accordingly, subsequent processing can be performed as in the endoscope system 10 according to the first embodiment.

Note that in the above embodiments, the present invention is applied to an endoscope system that performs processing on an endoscope image, which is one of medical images. However, the present invention is also applicable to a medical image processing system that performs processing on a medical image other than the endoscope image. In addition, the present invention is also applicable to a diagnosis supporting device for performing diagnosis support for a user by using a medical image. Furthermore, the present invention is also applicable to a medical service supporting device for supporting a medical service such as a diagnosis report by using a medical image.

In the above embodiments, a hardware configuration of processing units that perform various kinds of processing, such as the usual mode processing unit 62, the biological information measurement mode processing unit 64, the oxygen saturation processing unit 70, the reference value processing unit 72, the reference value processing unit 130, the reference value processing unit 150, and the reference value processing unit 180, is any of the following various processors. Various processors include a central processing unit (CPU) that is a general-purpose processor functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute various kinds of processing, and the like.

One processing unit may be constituted by one of these various processors, or may be constituted by two or more processors of the same type or different types in combination (e.g., a combination of a plurality of FPGAs or a combination of a CPU and an FPGA). In addition, a plurality of processing units may be constituted by one processor. As a first example for constituting a plurality of processing units with one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one integrated circuit (IC) chip, as typified by a system on chip (SoC) or the like. In this manner, various processing units are constituted by one or more of the above various processors in terms of hardware configuration.

More specifically, the hardware configuration of these various processors is electric circuitry constituted by combining circuit elements such as semiconductor elements.

REFERENCE SIGNS LIST 10 endoscope system
12 endoscope
14 light source device
16 processor device
17 universal cord
18 monitor
20 user interface
21 insertion part
22 operating unit
22a angle knob
22b mode switching SW
22c zoom operating unit
23 bending part
24 tip part
24a illumination optical system
24b imaging optical system
34 first blue laser light source
36 second blue laser light source
40 light source control unit
41 light guide
44 fluorescent body
45 illumination lens
46 imaging lens 47 zoom lens
48 sensor
49 imaging control unit
50 CDS/AGC circuit
52 A/D converter
54 image acquiring unit
56 digital signal processor (DSP)
58 noise reduction unit
60 image processing switching unit
62 usual mode processing unit
64 biological information measurement mode processing unit
66 display control unit
70 oxygen saturation processing unit
72 reference value processing unit
73 image storage unit
74 alignment processing unit
76 light amount ratio correcting unit
78 signal ratio calculating unit
80 correlation storage unit
82 oxygen saturation calculating unit
83 oxygen saturation image generating unit
84 measurement region setting unit
85 measurement value calculating unit
86 graph
87 graph
88 lower limit line
89 upper limit line
90 "+" button
91 "−" button
92 reference value calculation region setting unit
94 reliability calculating unit
95 region appropriateness determining unit
96 first reference value calculating unit
97 error generating unit
98 region setting prohibition control unit
110 reference value processing unit
111 reliability calculating unit
112 second reference value calculating unit
114 high reliability region setting unit
116 first candidate reference value calculating unit
118 first reference value selecting unit
130 reference value processing unit
132 biological information frequency distribution calculating unit
134 third reference value calculating unit
136 first region excluding distribution setting unit
138 second candidate reference value calculating unit
140 second reference value selecting unit
142, 144, 146 first region excluding distribution
150 reference value processing unit
152 arithmetic value frequency distribution calculating unit
154 fourth reference value calculating unit
156 second region excluding distribution setting unit
158 third candidate reference value calculating unit
160 third reference value selecting unit
162, 164, 166 second region excluding distribution
180 reference value processing unit
182 user setting unit
183 reliability calculating unit
184 reference value input screen
186 reference value input screen
187 "+" button
188 "−" button
190 slide bar
192 slider
194 reference value input screen
300 endoscope system
301 light emitting diode (LED) light source unit
302 high-pass filter (HPF)
303 inserting/removing unit
304 light source control unit
400 endoscope system
401 broadband light source
402 rotating filter
403 rotating filter control unit
405 sensor
410 usual observation mode filter
410a R filter
410b G filter
410c B filter
411 biological information measurement mode filter
411a R filter
411b G filter
411c B filter
411d narrowband filter

What is claimed is:

1. A medical image processing system comprising:
a processor configured to:
acquire an observation image obtained by imaging an observation target;
calculate, based on the observation image, biological information included in the observation target;
calculate, based on the observation image, reliability regarding the biological information;
set, for a measurement value indicative of the biological information of a measurement target in the observation target, a reference value serving as a reference for the biological information by using the reliability;
calculate a difference value between the measurement value and the reference value and generate, based on the difference value, a difference image;
generate, based on the biological information, a biological information image that is an image indicative of the biological information;
set a reference value calculation region that is a target for calculating the reference value in the observation image or the biological information image;
calculate, based on the biological information included in the reference value calculation region, the reference value;
determine that the reference value is appropriately set in the reference value calculation region if a representative value of the reliability included in the reference value calculation region is greater than or equal to a region determination threshold and determine that the reference value is not appropriately set in the reference value calculation region if the representative value of the reliability included in the reference value calculation region is less than the region determination threshold; and
generate, if it is determined that the reference value is not accurately set in the reference value calculation region, an error for reporting that the reference value is not accurately calculated.

2. The medical image processing system according to claim 1,
wherein the processor is further configured to automatically set, based on the reliability, the reference value calculation region.

3. The medical image processing system according to claim 1,
wherein the processor is further configured to perform region setting prohibition control to prohibit setting of the reference value calculation region for a low reliability region where the reliability is less than a first reliability threshold in the observation image or the biological information image.

4. The medical image processing system according to claim 3, wherein the processor is further configured to:
display the low reliability region on a display.

5. The medical image processing system according to claim 1,
wherein the reference value is a representative value of the biological information included in the reference value calculation region.

6. A medical image processing system comprising:
a processor configured to:
acquire an observation image obtained by imaging an observation target;
calculate, based on the observation image, biological information included in the observation target;
calculate, based on the observation image, reliability regarding the biological information;
set, for a measurement value indicative of the biological information of a measurement target in the observation target, a reference value serving as a reference for the biological information by using the reliability;
calculate a difference value between the measurement value and the reference value and generate, based on the difference value, a difference image;
generate, based on the biological information, a biological information image that is an image indicative of the biological information;
set a reference value calculation region that is a target for calculating the reference value in the observation image or the biological information image;
calculate, based on the biological information included in the reference value calculation region, the reference value; and
multiply the biological information included in the reference value calculation region by a weighting factor based on the reliability and perform addition to calculate the reference value.

7. The medical image processing system according to claim 1,
wherein the processor is further configured to multiply the biological information by a weighting factor based on the reliability and perform addition to calculate the reference value.

8. The medical image processing system according to claim 1,
wherein the processor is further configured to:
set a plurality of high reliability regions in which the reliability is greater than or equal to each of second reliability thresholds, the second reliability thresholds being different from each other and set in advance; and
calculate candidate reference values serving as candidates for the reference value from the biological information included in the respective high reliability regions.

9. The medical image processing system according to claim 8, wherein the processor is further configured to:
display the high reliability regions and the candidate reference values corresponding to the high reliability regions on a display; and
select the reference value from among the candidate reference values displayed on the display.

10. A medical image processing system comprising:
a processor configured to:
acquire an observation image obtained by imaging an observation target;
calculate, based on the observation image, biological information included in the observation target;
set, for a measurement value indicative of the biological information of a measurement target in the observation target, a reference value serving as a reference for the biological information;
calculate a difference value between the measurement value and the reference value and generate, based on the difference value, a difference image; and
calculate a frequency distribution of the biological information,
wherein the processor is further configured to calculate, based on a first region excluding distribution, the reference value, the first region excluding distribution excluding a first distribution region where reliability of the biological information is low in the frequency distribution of the biological information.

11. The medical image processing system according to claim 10,
wherein processor is further configured to:
set a plurality of first region excluding distributions excluding a plurality of first distribution regions from the frequency distribution of the biological information, the first distribution regions being set where the reliability of the biological information is low in the frequency distribution of the biological information; and
calculate, based on the first region excluding distributions, candidate reference values serving as candidates for the reference value.

12. The medical image processing system according to claim 11, wherein the processor is further configured to:
display the first region excluding distributions and the candidate reference values corresponding to the first region excluding distributions on a display; and
select the reference value from among the candidate reference values displayed on the display.

13. A medical image processing system comprising:
a processor configured to:
acquire observation images in a plurality of frames obtained by imaging an observation target in different frames;
calculate an arithmetic value through arithmetic processing based on the observation images in the plurality of frames and calculate, from the calculated arithmetic value, biological information included in the observation target;
set, for a measurement value indicative of the biological information of a measurement target in the observation target, a reference value serving as a reference for the biological information by using reliability of the biological information;
calculate a difference value between the measurement value and the reference value and generate, based on the difference value, a difference image; and
calculate a frequency distribution of the arithmetic value, wherein the processor is further configured to use the arithmetic value as the reliability, and calculate, based on a second region excluding distribution, the reference value, the second region excluding distribution excluding a second distribution region having a specific arithmetic value in the frequency distribution of the arithmetic value.

14. The medical image processing system according to claim 13,
wherein the processor is further configured to:
set a plurality of second region excluding distributions excluding a plurality of second distribution regions from the frequency distribution of the arithmetic value, the second distribution regions being set and having the specific arithmetic value in the frequency distribution of the arithmetic value; and
calculate, based on the second region excluding distributions, candidate reference values serving as candidates for the reference value.

15. The medical image processing system according to claim 14, wherein the processor is further configured to:
display the second region excluding distributions and the candidate reference values corresponding to the second region excluding distributions on a display; and
select the reference value from among the candidate reference values displayed on the display.

16. The medical image processing system according to claim 1,
wherein the processor is further configured to:
set the reference value by using a user interface, and
wherein the reference value is adjusted by using the reliability.

17. The medical image processing system according to claim 1, wherein the processor is further configured to:
set a region of the measurement target as a measurement target region in the observation image or the observation images or the biological information image; and
calculate, based on the biological information included in the measurement target region, the measurement value.

18. An endoscope system comprising:
a processor configured to:
obtain an observation image by imaging an observation target;
acquire the observation image obtained by imaging the observation target;
calculate, based on the observation image, biological information included in the observation target;
calculate, based on the observation image, reliability regarding the biological information;
set, for a measurement value indicative of the biological information of a measurement target in the observation target, a reference value serving as a reference for the biological information by using the reliability;
calculate a difference value between the measurement value and the reference value and generate, based on the difference value, a difference image;
generate, based on the biological information, a biological information image that is an image indicative of the biological information;
set a reference value calculation region that is a target for calculating the reference value in the observation image or the biological information image;
calculate, based on the biological information included in the reference value calculation region, the reference value;
determine that the reference value is appropriately set in the reference value calculation region if a representative value of the reliability included in the reference value calculation region is greater than or equal to a region determination threshold and determine that the reference value is not appropriately set in the reference value calculation region if the representative value of the reliability included in the reference value calculation region is less than the region determination threshold; and
generate, if it is determined that the reference value is not accurately set in the reference value calculation region, an error for reporting that the reference value is not accurately calculated.

19. An endoscope system comprising:
a processor configured to:
acquire an observation image obtained by imaging an observation target;
calculate, based on the observation image, biological information included in the observation target;
calculate, based on the observation image, reliability regarding the biological information;
set, for a measurement value indicative of the biological information of a measurement target in the observation target, a reference value serving as a reference for the biological information by using the reliability;
calculate a difference value between the measurement value and the reference value and generate, based on the difference value, a difference image;
generate, based on the biological information, a biological information image that is an image indicative of the biological information;
set a reference value calculation region that is a target for calculating the reference value in the observation image or the biological information image;
calculate, based on the biological information included in the reference value calculation region, the reference value; and
multiply the biological information included in the reference value calculation region by a weighting factor based on the reliability and perform addition to calculate the reference value.

* * * * *